(12) United States Patent
Bourane et al.

(10) Patent No.: US 10,889,768 B2
(45) Date of Patent: Jan. 12, 2021

(54) HIGH SEVERITY FLUIDIZED CATALYTIC CRACKING SYSTEMS AND PROCESSES FOR PRODUCING OLEFINS FROM PETROLEUM FEEDS

(71) Applicant: Saudi Arabian Oil Company, Dhahran (SA)

(72) Inventors: Abdennour Bourane, Dhahran (SA); Raed Abudawoud, Khobar (SA); Ibrahim Abba, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/244,181

(22) Filed: Jan. 10, 2019

(65) Prior Publication Data

US 2019/0225894 A1 Jul. 25, 2019

Related U.S. Application Data

(60) Provisional application No. 62/621,698, filed on Jan. 25, 2018.

(51) Int. Cl.
*C10G 51/06* (2006.01)
*C10G 55/08* (2006.01)
(Continued)

(52) U.S. Cl.
CPC .............. *C10G 51/06* (2013.01); *B01J 8/003* (2013.01); *B01J 8/0015* (2013.01); *B01J 8/085* (2013.01);
(Continued)

(58) Field of Classification Search
CPC ..................................................... C10G 51/06
See application file for complete search history.

(56) References Cited

U.S. PATENT DOCUMENTS

| 977,228 A | 11/1910 | Schestopol |
| 3,074,878 A | 1/1963 | Pappas |
| (Continued) | | |

FOREIGN PATENT DOCUMENTS

| CN | 1710029 A | 12/2005 |
| CN | 102925210 A | 2/2013 |
| (Continued) | | |

OTHER PUBLICATIONS

Corma et al., "Steam catalytic cracking of naphtha over ZSM-5 zeolite for production of propene and ethene: Micro and mascroscopic implications of the presence of steam", Applied Catalysis A: General 417-418, pp. 220-235, 2012.
(Continued)

*Primary Examiner* — In Suk C Bullock
*Assistant Examiner* — Alyssa L Cepluch
(74) *Attorney, Agent, or Firm* — Dinsmore & Shohl LLP

(57) ABSTRACT

Systems and processes are disclosed for producing petrochemical products, such as ethylene, propene and other olefins from crude oil in high severity fluid catalytic cracking (HSFCC) units. Processes include separating a crude oil into a light fraction and a heavy fraction, cracking the light fraction and heavy fraction in separation cracking reaction zones, and regenerating the cracking catalysts in a two-zone regenerator having a first regeneration zone for the first catalyst (heavy fraction) and a second regeneration zone for the second catalyst (light fraction) separate from the first regeneration zone. Flue gas from the first catalyst regeneration zone is passed to the second regeneration zone to provide additional heat to raise the temperature of the second catalyst of the light fraction side. The disclosed systems and processes enable different catalysts and operating conditions to be utilized for the light fraction and the heavy fraction of a crude oil feed.

19 Claims, 4 Drawing Sheets

(51) Int. Cl.
*C07C 4/06* (2006.01)
*B01J 8/26* (2006.01)
*B01J 8/00* (2006.01)
*B01J 8/18* (2006.01)
*B01J 8/20* (2006.01)
*C10G 11/18* (2006.01)
*B01J 8/08* (2006.01)

(52) U.S. Cl.
CPC ............. *B01J 8/1827* (2013.01); *B01J 8/20* (2013.01); *B01J 8/26* (2013.01); *C07C 4/06* (2013.01); *C10G 11/182* (2013.01); *C10G 11/185* (2013.01); *C10G 11/187* (2013.01); *C10G 55/08* (2013.01); *B01J 2208/00752* (2013.01); *B01J 2208/00761* (2013.01); *C07C 2529/08* (2013.01); *C07C 2529/40* (2013.01); *C10G 2300/107* (2013.01); *C10G 2300/1044* (2013.01); *C10G 2300/1077* (2013.01); *C10G 2300/70* (2013.01); *C10G 2400/20* (2013.01); *C10G 2400/22* (2013.01)

(56) References Cited

U.S. PATENT DOCUMENTS

| | | |
|---|---|---|
| 3,835,029 A | 9/1974 | Larson |
| 3,837,822 A | 9/1974 | Ward |
| 3,856,659 A | 12/1974 | Owen |
| 3,888,762 A | 6/1975 | Gerhold |
| 4,090,949 A | 5/1978 | Owen et al. |
| 4,297,203 A | 10/1981 | Ford et al. |
| 4,419,221 A | 12/1983 | Castagnos et al. |
| 4,436,613 A | 3/1984 | Sayles et al. |
| 4,606,810 A | 8/1986 | Krambeck et al. |
| 4,830,728 A | 5/1989 | Herbst et al. |
| 4,980,053 A | 12/1990 | Li et al. |
| 4,992,160 A | 2/1991 | Long et al. |
| 5,026,935 A | 6/1991 | Leyshon et al. |
| 5,026,936 A | 6/1991 | Leyshon et al. |
| 5,043,522 A | 8/1991 | Leyshon et al. |
| 5,154,818 A | 10/1992 | Harandi et al. |
| 5,158,919 A * | 10/1992 | Haddad ............. B01J 23/90 208/113 |
| 5,160,424 A | 11/1992 | Le et al. |
| 5,171,921 A | 12/1992 | Gaffney et al. |
| 5,232,580 A | 8/1993 | Le et al. |
| 5,232,675 A | 8/1993 | Shu et al. |
| 5,318,689 A | 6/1994 | Hsing et al. |
| 5,326,465 A | 7/1994 | Yongqing et al. |
| 5,334,554 A | 8/1994 | Lin et al. |
| 5,372,704 A | 12/1994 | Harandi et al. |
| 5,380,690 A | 1/1995 | Zhicheng et al. |
| 5,451,313 A | 9/1995 | Wegerer et al. |
| 5,462,652 A | 10/1995 | Wegerer |
| 5,523,502 A | 6/1996 | Rubin |
| 5,549,813 A | 8/1996 | Dai et al. |
| 5,589,139 A | 12/1996 | Zinke et al. |
| 5,597,537 A | 1/1997 | Wegerer et al. |
| 5,637,207 A | 6/1997 | Hsing et al. |
| 5,670,037 A | 9/1997 | Zaiting et al. |
| 5,685,972 A | 11/1997 | Timken et al. |
| 5,730,859 A | 3/1998 | Johnson et al. |
| 5,770,042 A | 6/1998 | Galperin et al. |
| 5,858,207 A | 1/1999 | Lomas |
| 5,904,837 A | 5/1999 | Fujiyama |
| 5,951,850 A | 9/1999 | Ino et al. |
| 5,976,356 A | 11/1999 | Drake et al. |
| 5,993,642 A | 11/1999 | Mohr et al. |
| 6,015,933 A | 1/2000 | Abrevaya et al. |
| 6,069,287 A | 5/2000 | Ladwig et al. |
| 6,210,562 B1 | 4/2001 | Xie et al. |
| 6,287,522 B1 | 9/2001 | Lomas |
| 6,288,298 B1 | 9/2001 | Rodriguez et al. |
| 6,300,537 B1 | 10/2001 | Strohmaier et al. |
| 6,315,890 B1 | 11/2001 | Ladwig et al. |
| 6,420,621 B1 | 7/2002 | Sha et al. |
| 6,455,750 B1 | 9/2002 | Steffens et al. |
| 6,521,563 B2 | 2/2003 | Strohmaier et al. |
| 6,548,725 B2 | 4/2003 | Froment et al. |
| 6,566,293 B1 | 5/2003 | Vogt et al. |
| 6,602,403 B1 | 8/2003 | Steffens et al. |
| 6,652,737 B2 | 11/2003 | Touvelle et al. |
| 6,656,345 B1 | 12/2003 | Chen et al. |
| 6,656,346 B2 | 12/2003 | Ino et al. |
| 6,784,329 B2 | 8/2004 | O'Rear et al. |
| 6,867,341 B1 | 3/2005 | Abrevaya et al. |
| 6,979,755 B2 | 12/2005 | O'Rear et al. |
| 7,019,187 B2 | 3/2006 | Powers |
| 7,029,571 B1 | 4/2006 | Bhattacharyya et al. |
| 7,087,154 B2 | 8/2006 | Pinho et al. |
| 7,087,155 B1 | 8/2006 | Dath et al. |
| 7,128,827 B2 | 10/2006 | Tallman et al. |
| 7,153,479 B2 | 12/2006 | Peterson et al. |
| 7,169,293 B2 | 1/2007 | Lomas et al. |
| 7,220,351 B1 | 5/2007 | Pontier et al. |
| 7,261,807 B2 | 8/2007 | Henry et al. |
| 7,270,739 B2 | 9/2007 | Chen et al. |
| 7,312,370 B2 | 12/2007 | Pittman et al. |
| 7,314,964 B2 | 1/2008 | Abrevaya et al. |
| 7,326,332 B2 | 2/2008 | Chen et al. |
| 7,374,660 B2 | 5/2008 | Steffens et al. |
| 7,459,596 B1 | 12/2008 | Abrevaya et al. |
| 7,479,218 B2 | 1/2009 | Letzsch |
| 7,686,942 B2 | 3/2010 | Xie et al. |
| 7,906,077 B2 | 3/2011 | Sandacz |
| 7,935,654 B2 | 5/2011 | Choi et al. |
| 8,137,533 B2 | 3/2012 | Towler et al. |
| 8,247,631 B2 | 8/2012 | Nicholas et al. |
| 8,614,160 B2 | 12/2013 | Upson et al. |
| 8,864,979 B2 | 10/2014 | Palmas |
| 8,933,286 B2 | 1/2015 | Souza et al. |
| 9,096,806 B2 | 8/2015 | Abba et al. |
| 9,101,854 B2 | 8/2015 | Koseoglu et al. |
| 9,290,705 B2 | 3/2016 | Bourane et al. |
| 9,783,749 B2 | 10/2017 | Davydov |
| 9,816,037 B2 | 11/2017 | Avais |
| 2001/0042700 A1 | 11/2001 | Swan, III et al. |
| 2001/0056217 A1 | 12/2001 | Froment et al. |
| 2002/0003103 A1 | 1/2002 | Henry et al. |
| 2003/0220530 A1 | 11/2003 | Boelt et al. |
| 2005/0070422 A1 | 3/2005 | Chen et al. |
| 2006/0108260 A1 | 5/2006 | Henry |
| 2008/0011644 A1 | 1/2008 | Dean et al. |
| 2008/0011645 A1 | 1/2008 | Dean |
| 2008/0044611 A1 | 2/2008 | Husemann et al. |
| 2009/0112035 A1 | 4/2009 | Choi et al. |
| 2009/0288990 A1 | 11/2009 | Xie et al. |
| 2012/0241359 A1 * | 9/2012 | Al-Thubaiti ............. B01J 8/26 208/61 |
| 2013/0001130 A1 | 1/2013 | Mo |
| 2013/0172643 A1 | 7/2013 | Pradeep et al. |
| 2013/0248420 A1 | 9/2013 | Palmas |
| 2014/0110308 A1 | 4/2014 | Bourane et al. |
| 2014/0228205 A1 | 8/2014 | Narayanaswamy et al. |
| 2015/0094511 A1 | 4/2015 | Bastianti et al. |
| 2018/0305623 A1 | 10/2018 | Al-Ghrami et al. |
| 2018/0346827 A1 | 12/2018 | Al-Ghamdi et al. |
| 2019/0225894 A1 | 7/2019 | Bourane et al. |

FOREIGN PATENT DOCUMENTS

| | | |
|---|---|---|
| EP | 315179 A1 | 5/1989 |
| EP | 2688982 A1 | 1/2014 |
| GB | 978576 | 12/1964 |
| WO | 2010053482 A1 | 5/2010 |
| WO | 2012128973 A1 | 9/2012 |

OTHER PUBLICATIONS

International Search Report and Written Opinion dated Apr. 4, 2019 pertaining to International application No. PCT/US2019/013978 filed Jan. 17, 2019, 19 pgs.

(56) References Cited

OTHER PUBLICATIONS

Corma, "A new continuous laboratory reactor for the study of catalytic cracking", Applied Catalysis A: General 232, pp. 247-263, 2002.
International Search Report and Written Opinion pertaining to International Application PCT/US2018/030858 dated May 3, 2018.
Corma et al., "Different process schemes for converting light straight run and fluid catalytic cracing naphthas in a FCC unit for maximum propylene production", Applied Catalyst A: General 265, pp. 195-206, 2004.
Verstraete et al., "Study of direct and indirect naphtha recycling to a resid FCC unit for maximum propylene production", Catalysis Today, 106, pp. 62-71, 2005.
Examination Report pertaining to Application No. GC2018-35391 dated Nov. 27, 2019.
Office Action dated May 13, 2020 pertaining to U.S. Appl. No. 15/945,362, filed Apr. 4, 2018, 55 pgs.

* cited by examiner

HIGH SEVERITY FLUIDIZED CATALYTIC CRACKING SYSTEMS AND PROCESSES FOR PRODUCING OLEFINS FROM PETROLEUM FEEDS

CROSS-REFERENCE TO RELATED APPLICATION

This application claims the benefit of priority under 35 U.S.C. § 120 of U.S. Provisional Application No. 62/621,698, entitled "High Severity Fluidized Catalytic Cracking Systems and Processes for Producing Olefins from Petroleum Feeds," filed Jan. 25, 2018, the entire contents of which are incorporated by reference in this disclosure.

TECHNICAL FIELD

Embodiments of the present disclosure generally relate to fluid catalytic cracking processes, and more specifically relate to catalyst regeneration processes and systems used in high severity fluid catalytic cracking (HSFCC) systems.

BACKGROUND

Ethylene, propene, butenes, butadiene, and aromatics compounds such as benzene, toluene and xylenes are basic intermediates for a large proportion of the petrochemical industry. They are usually obtained through the thermal cracking (or steam pyrolysis) of petroleum gases and distillates such as naphtha, kerosene or even gas oil. These compounds are also produced through a refinery fluidized catalytic cracking (FCC) process where classical heavy feedstocks such as gas oils or residues are converted. Conventional FCC feedstocks range from hydrocracked bottoms to heavy feed fractions such as vacuum gas oil and atmospheric residue; however, these feedstocks are limited. The second most important source for propene production is currently refinery propene from FCC units. With the ever growing demand, FCC unit owners look increasingly to the petrochemicals market to boost their revenues by taking advantage of economic opportunities that arise in the propene market.

The worldwide increasing demand for light olefins remains a major challenge for many integrated refineries. In particular, the production of some valuable light olefins such as ethylene, propene, and butenes has attracted increased attention as pure olefin streams are considered the building blocks for polymer synthesis. The production of light olefins depends on several process variables like the feed type, operating conditions, and the type of catalyst. Despite the options available for producing a greater yield of propene and light olefins, intense research activity in this field is still being conducted. These options include the use of HSFCC systems, developing more selective catalysts for the process, and enhancing the configuration of the process in favor of more advantageous reaction conditions and yields. The HSFCC process is capable of producing yields of propene up to four times greater than the traditional fluid catalytic cracking unit and greater conversion levels for a range of petroleum steams.

SUMMARY

Embodiments of the present disclosure are directed to improved HSFCC systems and processes for producing one or more petrochemical products from a hydrocarbon material, such as a crude oil.

According to some embodiments, a process for producing petrochemical products from a hydrocarbon material comprises separating the hydrocarbon material into a lesser boiling point fraction and a greater boiling point fraction, cracking at least a portion of the greater boiling point fraction in the presence of a first catalyst at a reaction temperature of from 500° C. to 700° C. to produce a first cracking reaction product and a spent first catalyst, and cracking at least a portion of the lesser boiling point fraction in the presence of a second catalyst at a reaction temperature of from 500° C. to 700° C. to produce a second cracking reaction product and a spent second catalyst. The process further comprises separating at least a portion of the first cracking reaction product from the spent first catalyst and separating at least a portion of the second cracking reaction product from the spent second catalyst. Additionally, the process comprises regenerating at least a portion of the spent first catalyst to produce a regenerated first catalyst, maintaining the spent second catalyst separate from the spent first catalyst, transferring heat from regeneration of the spent first catalyst to the spent second catalyst, and regenerating at least a portion of the spent second catalyst to produce a regenerated second catalyst. The process further comprises recovering the first cracking reaction product and the second cracking reaction product.

According to one or more other embodiments, a process for operating a hydrocarbon feed conversion system having a first fluidic catalytic cracking (FCC) unit and a second FCC unit for producing petrochemical products from a hydrocarbon feed stream is disclosed. The process comprises introducing the hydrocarbon feed stream to a feed separator, separating the hydrocarbon feed stream into a lesser boiling point fraction and a greater boiling point fraction in the feed separator, passing the greater boiling point fraction to the first FCC unit, cracking at least a portion of the greater boiling point fraction in the first FCC unit in the presence of a first catalyst at a reaction temperature of from 500° C. to 700° C. to produce a first cracking reaction product and a spent first catalyst, passing the lesser boiling point fraction to the second FCC unit, and cracking at least a portion of the lesser boiling point fraction in the second FCC unit in the presence of a second catalyst and at a reaction temperature of from 500° C. to 700° C. to produce a second cracking reaction product and a spent second catalyst. The process further comprises passing the spent first catalyst to a first regeneration zone, regenerating at least a portion of the spent first catalyst in the first regeneration zone to produce a regenerated first catalyst, passing the spent second catalyst to a second regeneration zone separate from the first regeneration zone, and regenerating at least a portion of the spent second catalyst in the second regeneration zone to produce a regenerated second catalyst. The process includes transferring heat from the first regeneration zone to the second regeneration zone, and recycling the regenerated first catalyst to the first FCC unit and the regenerated second catalyst to the second FCC unit. The process further comprises recovering the first cracking reaction product and the second cracking reaction product.

According to yet other embodiments, a system for producing petrochemical products from a hydrocarbon feed stream comprises a first cracking reaction zone, a first separation zone downstream of the first cracking reaction zone, and a first regeneration zone downstream of the first separation zone. The system also comprises a second cracking reaction zone in parallel with the first cracking reaction zone, a second separation zone downstream of the second cracking reaction zone, and a second regeneration zone downstream of the second separation zone, where the second regeneration zone is physically separated from the first regeneration zone. A flue gas flow path extends from the first regeneration zone to the second regeneration zone, the flue gas flow path comprising a particulate barrier for preventing a transfer of one or more spent catalysts between the first regeneration zone and the second regeneration zone.

According to still other embodiments, a process for producing one or more petrochemical products from a hydrocarbon feed stream comprises separating the hydrocarbon feed stream into a lesser boiling point fraction and a greater boiling point fraction, cracking the greater boiling point fraction in a first fluid catalytic cracking (FCC) unit in the presence of a first catalyst and at a reaction temperature of from 500° C. to 700° C. to produce a first cracking reaction product, and cracking the lesser boiling point fraction in a second FCC unit in the presence of a second catalyst and at a reaction temperature of from 500° C. to 700° C. to produce a second cracking reaction product, the second FCC unit operated in parallel with the first FCC unit. The process further includes regenerating the first catalyst in a first regeneration zone, transferring heat from the first regeneration zone to the second regeneration zone, and regenerating the second catalyst in a second regeneration zone separate from the first regeneration zone. The process further includes recycling the first catalyst back to the first FCC unit and the second catalyst back to the second FCC unit, and recovering the first cracking reaction product and the second cracking reaction product.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 2:
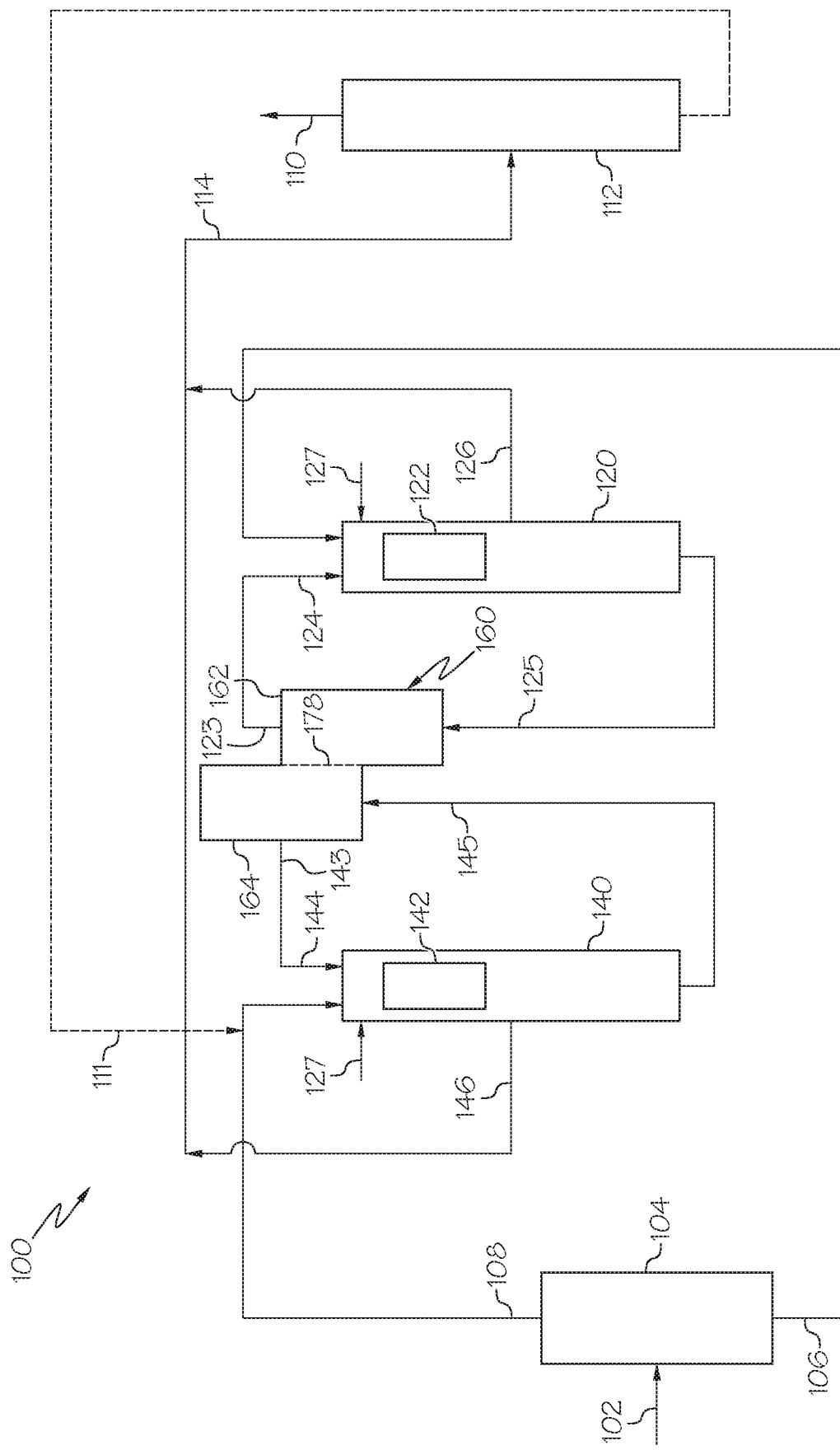
FIG. 2 is a generalized schematic diagram of an embodiment of a hydrocarbon feed conversion system, according to one or more embodiments described in this disclosure.
Figure 3:
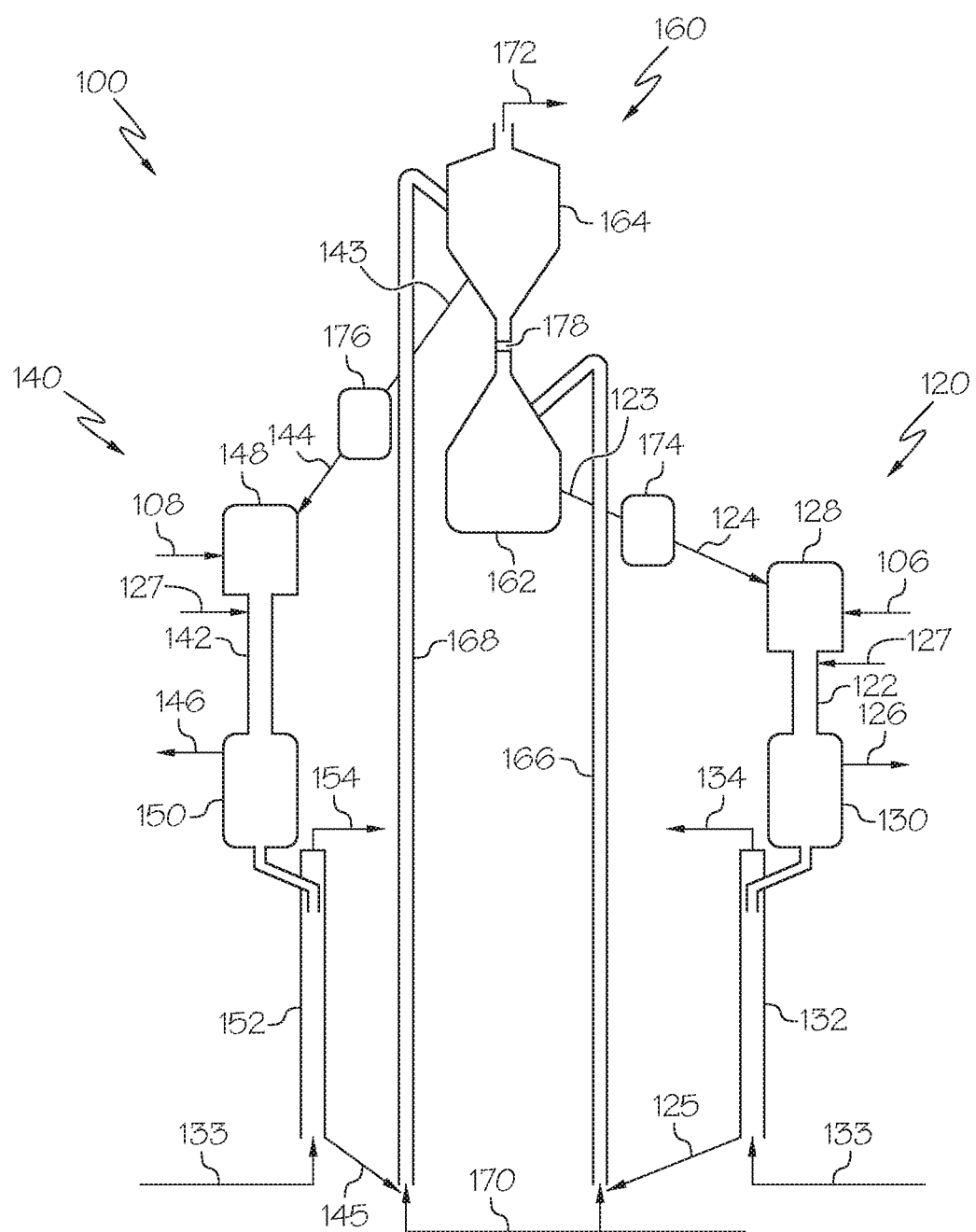
FIG. 3 depicts a generalized schematic diagram of another embodiment of a hydrocarbon feed conversion system, according to one or more embodiments described in this disclosure.

For the purpose of describing the simplified schematic illustrations and descriptions of FIGS. 2-3, the numerous valves, temperature sensors, electronic controllers and the like that may be employed and well known to those of ordinary skill in the art of certain chemical processing operations are not included. Further, accompanying components that are often included in conventional chemical processing operations, such as refineries, such as, for example, air supplies, catalyst hoppers, and flue gas handling are not depicted. It should be understood that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines which may serve to transfer process streams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows which do not connect two or more system components signify a product stream which exits the depicted system or a system inlet stream which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a system product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagrams of FIGS. 2-3. Mixing or combining may also include mixing by directly introducing both streams into a like reactor, separation device, or other system component. For example, it should be understood that when two streams are depicted as being combined directly prior to entering a separation unit or reactor, that in some embodiments the streams could equivalently be introduced into the separation unit or reactor and be mixed in the reactor.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to systems and processes for converting one or more hydrocarbon feed streams into one or more petrochemical products using a high severity fluidized catalytic cracking (HSFCC) system that includes two downflow fluid catalytic cracking (FCC) units operated at high severity conditions. The hydrocarbon feed stream is separated into a lesser boiling point fraction and a greater boiling point fraction.

The greater boiling point fraction is introduced to a first cracking reaction zone, in which the greater boiling point fraction is mixed with a first catalyst and cracked to produce a first cracking reaction product. The lesser boiling point fraction is introduced to a second cracking reaction zone, in which the lesser boiling point fraction is mixed with a second catalyst and cracked to produce a second cracking reaction product. The first and second cracking reaction zones share a regenerator having two regeneration zones, which are separated from one another so that a first catalyst moving through a first regeneration zone is maintained separate from a second catalyst moving through the second regeneration zone. The first catalyst is separated from the first cracking reaction product and introduced to the first regeneration zone, and the second catalyst is separated from the second cracking reaction product and introduced to the second regeneration zone. Flue gas generated from regeneration of the first catalyst in the first regeneration zone may be transferred to the second regeneration zone, where the flue gas may transfer heat to the second catalyst to raise the temperature of the second catalyst to or above the cracking reaction temperature in the second cracking reaction zone.

As used in this disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors such as fixed bed reactors, and fluidized bed reactors. One or more "reaction zones" may be disposed in a reactor. As used in this disclosure, a "reaction zone" refers to an area where a particular reaction takes place in a reactor. For example, a packed bed reactor with multiple catalyst beds may have multiple reaction zones, where each reaction zone is defined by the area of each catalyst bed.

As used in this disclosure, a "separation unit" refers to any separation device that at least partially separates one or more chemicals that are mixed in a process stream from one another. For example, a separation unit may selectively separate differing chemical species from one another, forming one or more chemical fractions. Examples of separation units include, without limitation, distillation columns, flash drums, knock-out drums, knock-out pots, centrifuges, cyclones, filtration devices, traps, scrubbers, expansion devices, membranes, solvent extraction devices, and the like. It should be understood that separation processes described in this disclosure may not completely separate all of one chemical constituent from all of another chemical constituent. It should be understood that the separation processes described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separation unit and be divided, or separated, into two or more process streams of desired composition. Further, in some separation processes, a "lesser boiling point fraction" (sometimes referred to as a "light fraction") and a "greater boiling point fraction" (sometimes referred to as a "heavy fraction") may exit the separation unit, where, on average, the contents of the lesser boiling point fraction stream have a lesser boiling point than the greater boiling point fraction stream. Other streams may fall between the lesser boiling point fraction and the greater boiling point fraction, such as an "intermediate boiling point fraction."

As used in this disclosure, the term "high severity conditions" generally refers to FCC temperatures of 500° C. or greater and ratios of catalyst to oil of 5:1 by weight or greater, both of which may be greater than typical FCC reaction conditions.

It should be understood that an "effluent" generally refers to a stream that exits a system component such as a separation unit, a reactor, or reaction zone, following a particular reaction or separation, and generally has a different composition (at least proportionally) than the stream that entered the separation unit, reactor, or reaction zone.

As used in this disclosure, a "catalyst" refers to any substance which increases the rate of a specific chemical reaction. Catalysts described in this disclosure may be utilized to promote various reactions, such as, but not limited to, cracking (including aromatic cracking), demetalization, desulfurization, and, denitrogenation. As used in this disclosure, "cracking" generally refers to a chemical reaction where a molecule having carbon to carbon bonds is broken into more than one molecule by the breaking of one or more of the carbon to carbon bonds, or is converted from a compound which includes a cyclic moiety, such as a cycloalkane, cycloalkane, naphthalene, an aromatic or the like, to a compound which does not include a cyclic moiety or contains fewer cyclic moieties than prior to cracking.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "flue gas stream" passing from a first system component to a second system component should be understood to equivalently disclose "flue gas" passing from a first system component to a second system component.

The hydrocarbon feed stream generally comprises a hydrocarbon material. In embodiments, the hydrocarbon material of the hydrocarbon feed stream may be crude oil. As used herein, the term "crude oil" is to be understood to mean a mixture of petroleum liquids and gases, including impurities such as sulfur-containing compounds, nitrogen-containing compounds and metal compounds, as distinguished from fractions of crude oil. In certain embodiments the crude oil feedstock is a minimally treated light crude oil to provide a crude oil feedstock having total metals (Ni+V) content of less than 5 ppm and Conradson carbon residue of less than 5 wt %.

While the present description and examples may specify crude oil as the hydrocarbon material of the hydrocarbon feed stream 102, it should be understood that the hydrocarbon feed conversion systems 100 described with respect to the embodiments of FIGS. 2-3, respectively, are applicable for the conversion of a wide variety of hydrocarbon materials, which may be present in the hydrocarbon feed stream 102, including, but not limited to, crude oil, vacuum residue, tar sands, bitumen, atmospheric residue, vacuum gas oils, demetalized oils, naphtha streams, other hydrocarbon streams, or combinations of these materials. The hydrocarbon feed stream 102 may include one or more non-hydrocarbon constituents, such as one or more heavy metals, sulphur compounds, nitrogen compounds, inorganic components, or other non-hydrocarbon compounds. If the hydrocarbon feed stream 102 is crude oil, it may have an American Petroleum Institute (API) gravity of from 22 degrees to 40 degrees. For example, the hydrocarbon feed stream 102 utilized may be an Arab heavy crude oil. Example properties for one particular exemplary grade of Arab heavy crude oil are provided subsequently in Table 1. It should be understood that, as used in this disclosure, a "hydrocarbon feed" may refer to a raw hydrocarbon material which has not been previously treated, separated, or otherwise refined (such as crude oil) or may refer to a hydrocarbon material which has undergone some degree of processing, such as treatment, separation, reaction, purifying, or other operation, prior to being introduced to the hydrocarbon feed conversion system 100 in the hydrocarbon feed stream 102.

TABLE 1

Example of Arab Heavy Export Feedstock

| Analysis | Units | Value |
|---|---|---|
| American Petroleum Institute (API) gravity | degree | 27 |
| Density | grams per cubic centimeter (g/cm³) | 0.8904 |
| Sulfur Content | weight percent (wt. %) | 2.83 |
| Nickel | parts per million by weight (ppmw) | 16.4 |
| Vanadium | ppmw | 56.4 |
| Sodium Chloride (NaCl) Content | ppmw | <5 |
| Conradson Carbon Residue (CCR) | wt. % | 8.2 |
| C₅ Asphaltenes | wt. % | 7.8 |
| C₇ Asphaltenes | wt. % | 4.2 |

Figure 1:
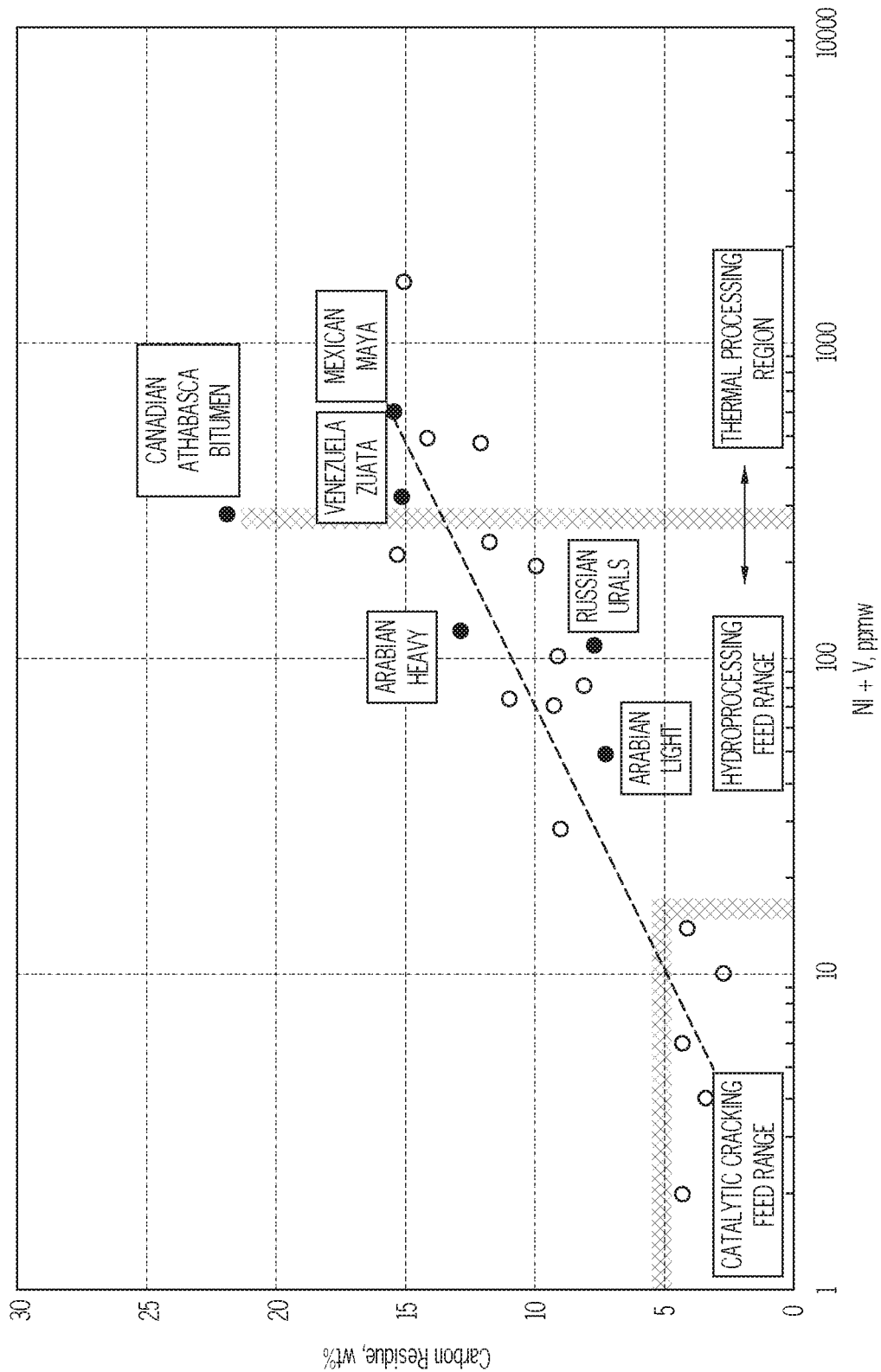
FIG. 1 graphically depicts relative properties of various hydrocarbon feed streams used for producing one or more petrochemical products, according to one or more embodiments described in this disclosure.

Referring to FIG. 1, various hydrocarbon feed streams to be converted in a conventional FCC process are generally required to satisfy certain criteria in terms of the metals content and the Conradson Carbon Residue (CCR) or Ramsbottom carbon content. The CCR of a feed material is a measurement of the residual carbonaceous materials that remain after evaporation and pyrolysis of the feed material. Greater metals content and CCR of a feed stream may lead to more rapid deactivation of the catalyst. For greater levels of CCR, more energy may be needed in the regeneration step to regenerate the catalyst. For example, certain hydrocarbon feeds, such as residual oils, contain refractory components such as polycyclic aromatics which are difficult to crack and promote coke formation in addition to the coke formed during the catalytic cracking reaction. Because of the greater levels of CCR of these certain hydrocarbon feeds, the burning load on the regenerator is increased to remove the coke and residue from the spent catalysts to transform the spent catalysts to regenerated catalysts. This requires modification of the regenerator to be able to withstand the increase burning load without experiencing material failure. In addition, certain hydrocarbon feeds to the FCC may contain large amounts of metals, such as nickel, vanadium, or other metals for example, which may rapidly deactivate the catalyst during the cracking reaction process.

In general terms, the hydrocarbon feed conversion system 100 includes two FCC units in each of which a portion of the hydrocarbon feed stream 102 contacts heated fluidized catalytic particles in a cracking reaction zone maintained at high severity temperatures and pressures. When the portion of the hydrocarbon feed stream 102 contacts the hot catalyst and is cracked to lighter products, carbonaceous deposits, commonly referred to as coke, form on the catalyst and deactivate the catalyst. The spent catalyst deactivated by the coke deposits is separated from the cracking reaction products, stripped of removable hydrocarbons, and passed to a regeneration process where the coke is burned from the catalyst in the presence of air to produce a regenerated catalyst that is catalytically effective. The term "catalytically effective" refers to the ability of the regenerated catalyst to enable cracking reactions. Following regeneration, the regenerated catalyst may have equal to or less than 1 wt. % coke based on the total weight of the regenerated catalyst. The combustion products are removed from the regeneration process as a flue gas stream. The heated regenerated catalysts are then recycled back to the cracking reaction zone of the FCC units.

Referring now to FIG. 2, a hydrocarbon feed conversion system 100 is schematically depicted. The hydrocarbon feed conversion system 100 is a high severity fluid catalytic cracking (HSFCC) system. The hydrocarbon feed conversion system 100 generally receives a hydrocarbon feed stream 102 and directly processes the hydrocarbon feed stream 102 to produce one or more system product streams 110.

Referring to FIG. 2, the hydrocarbon feed stream 102 is introduced to a feed separator 104 which separates the contents of the hydrocarbon feed stream 102 into a greater boiling point fraction stream 106 and a lesser boiling point fraction stream 108. In one or more embodiments, the feed separator 104 may be a vapor-liquid separator such as a flash drum (sometimes referred to as a breakpot, knock-out drum, knock-out pot, compressor suction drum, or compressor inlet drum). In embodiments that utilize a vapor-liquid separator as the feed separator 104, the lesser boiling point fraction stream 108 may exit the feed separator 104 as a vapor and the greater boiling point fraction stream 106 may exit the feed separator 104 as a liquid. The vapor-liquid separator may be operated at a temperature suitable to separate the hydrocarbon feed stream 102 into the greater boiling point fraction stream 106 and the lesser boiling point fraction stream 108. The temperature of the vapor-liquid separator may be from 180 degrees Celsius (° C.) to 400° C. For example, the contents of the lesser boiling point fraction stream 108 may have a boiling point of at least 180° C. and less than or equal to 400° C., less than or equal to 350° C., less than or equal to 300° C., less than or equal to 250° C., or less than or equal to 200° C. The contents of the greater boiling point fraction stream 106 may have a boiling point of less than or equal to 400° C. and at least 180° C., at least 200° C., at least 250° C., at least 300° C., or at least 350° C. The greater boiling point fraction stream 106 may also be equal to or greater than 3 wt. % micro carbon residue (MCR). The greater boiling point fraction stream 106 may have a specific gravity of equal to or greater than 0.88.

In one or more embodiments, the feed separator 104 may be a flashing column that may separate the hydrocarbon feed stream 102 into the greater boiling point fraction stream 106 and the lesser boiling point fraction stream 108. The flashing column may be operated at a flashing temperature that results in the lesser boiling point fraction stream 108 having less than 1 wt. % Conradson Carbon and less than 1 ppm total metals. The flashing column may be operated at a temperature of from 180° C. to 400° C. Alternatively, in other embodiments, the feed separator 104 may include at least one of a distillation device or a cyclonic vapor liquid separation device.

One or more supplemental feed streams (not shown) may be added to the hydrocarbon feed stream 102 prior to introducing the hydrocarbon feed stream 102 to the feed separator 104. As previously described, in one or more embodiments, the hydrocarbon feed stream 102 may be crude oil. In one or more embodiments, the hydrocarbon feed stream 102 may be crude oil, and one or more supplemental feed streams comprising one or more of a vacuum residue, tar sands, bitumen, atmospheric residue, vacuum gas oils, demetalized oils, naphtha streams, other hydrocarbon streams, or combinations of these materials, may be added to the crude oil upstream of the feed separator 104.

Although the present disclosure focuses on converting a hydrocarbon feed stream 102 that is a crude oil, the hydrocarbon feed stream 102 may alternatively comprise a plurality of refinery hydrocarbon streams output from one or more crude oil refinery operations. The plurality of refinery hydrocarbon streams may include a vacuum residue, an atmospheric residue, or a vacuum gas oil, for example. In some embodiments, the plurality of refinery hydrocarbon streams may be combined into the hydrocarbon feed stream 102. In these embodiments, the hydrocarbon feed stream 102 may be introduced to the feed separator 104 and separated into the greater boiling point fraction stream 106 and the lesser boiling point fraction stream 108. Alternatively, in some embodiments, the plurality of refinery hydrocarbon streams may be introduced directly to the first FCC unit 120 and the second FCC unit 140. For example, one or more heavy refinery hydrocarbon streams such as vacuum residues, atmospheric residues, or vacuum gas oils, for example, may be introduced directly to the first FCC unit 120 as the greater boiling point fraction stream 106, and other light refinery hydrocarbon streams, such as a naphtha stream for example, may be introduced directly to the second FCC unit 140 as the lesser boiling point fraction stream 108.

Referring to FIG. 2, the greater boiling point fraction stream 106 is passed to a first FCC unit 120 that includes a first cracking reaction zone 122. The greater boiling point fraction stream 106 is combined or mixed with a first catalyst 124 and cracked to produce a mixture of a spent first catalyst 125 and a first cracking reaction product stream 126. Steam 127 may be added to the first cracking reaction zone 122 to further increase the temperature in the first cracking reaction zone 122. The spent first catalyst 125 is separated from the first cracking reaction product 126 and passed to a first regeneration zone 162 of the regenerator 160, in which the spent first catalyst 125 is regenerated to produce a regenerated first catalyst 123. The regenerated first catalyst 123 is then passed back to the first cracking reaction zone 122 as the first catalyst 124.

The lesser boiling point fraction stream 108 is passed to a second FCC unit 140 that includes a second cracking reaction zone 142. The lesser boiling point fraction stream 108 is mixed with a second catalyst 144 and cracked to produce a second spent catalyst 145 and a second cracking reaction product 146. Steam 127 may also be added to the second cracking reaction zone 142 to increase the temperature in the second cracking reaction zone 142. The spent second catalyst 145 is separated from the second cracking reaction product 146 and passed to a second regeneration zone 164 of the regenerator 160, where the spent second catalyst 145 is regenerated to produce a regenerated second catalyst 143. The spent second catalyst 145 in the second regeneration zone 164 may be maintained separate from the spent first catalyst 125 in the first regeneration zone 162 by a porous separation zone 178 disposed between the first regeneration zone 162 and the second regeneration zone 164. The regenerated second catalyst 143 is then passed back to the second cracking reaction zone 142 as the second catalyst 144. The first cracking reaction zone 122 and the second cracking reaction zone 142 are operated in parallel.

The first cracking reaction product stream 126 and the second cracking reaction product stream 146 each include a mixture of cracked hydrocarbon materials, which may be further separated into one or more petrochemical products and recovered from the system in the one or more system product streams 110. For example, the first cracking reaction product stream 126 and the second cracking reaction product stream 146 may include one or more of cracked gas oil, cracked gasoline, cracked naphtha, mixed butenes, butadiene, propene, ethylene, methane, other petrochemical products, or combinations of these. The hydrocarbon feed conversion system 100 may include a product stream separator 112. The first cracking reaction product stream 126, the second cracking reaction product stream 146, or both the first and second cracking reaction product streams 126, 146 may be introduced to the product stream separator 112 to separate these streams into a plurality of system product streams 110, recycle streams 111, or both system product streams 110 and recycle streams 111. In one or more embodiments, the first cracking reaction product stream 126 and the second cracking reaction product stream 146 may be combined into a combined reaction product stream 114. The combined reaction product stream 114 may be introduced to the product separator 112. The product separator 112 may be fluidly coupled to the first separation zone 130, the second separation zone 150, or both the first separation zone 130 and the second separation zone 150.

Referring now to FIG. 3, the first FCC unit 120 may include a first catalyst/feed mixing zone 128, the first cracking reaction zone 122, a first catalyst separation zone 130, and a first stripping zone 132. The greater boiling point fraction stream 106 may be introduced to the first catalyst/feed mixing zone 128, where the greater boiling point fraction stream 106 may be mixed with the first catalyst 124. During steady state operation of the hydrocarbon feed conversion system 100, the first catalyst 124 is the regenerated first catalyst 123 that is passed to the first catalyst/feed mixing zone 128 from one or more first catalyst hoppers 174. The first catalyst hoppers 174 receive the regenerated first catalyst 123 from the regenerator 160 following regeneration of the spent first catalyst 125. At initial start-up of the hydrocarbon feed conversion system 100, the first catalyst 124 may include fresh first catalyst (not shown), which is first catalyst 124 that has not been circulated through the first FCC unit 120 and the regenerator 160. In embodiments, fresh first catalyst may also be introduced to first catalyst hopper 174 during operation of the hydrocarbon feed conversion system 100 so that the first catalyst 124 introduced to the first catalyst/feed mixing zone 128 comprises a mixture of fresh first catalyst and regenerated first catalyst 123. Fresh first catalyst may be introduced to the first catalyst hopper 174 periodically during operation to replenish lost first catalyst 124 or compensate for spent first catalyst 125 that becomes permanently deactivated, such as through heavy metal accumulation in the catalyst.

In one or more embodiments, one or more supplemental feed streams (not shown) may be combined with the greater boiling point fraction stream 106 before introduction of the greater boiling point fraction stream 106 to the first catalyst/feed mixing zone 128. In other embodiments, one or more supplemental feed streams may be added directly to the first catalyst/feed mixing zone 128, where the supplemental feed stream may be mixed with the greater boiling point fraction stream 106 and the first catalyst 124 prior to introduction into the first cracking reaction zone 122. As previously described, the supplemental feed stream may include one or more of vacuum residues, tar sands, bitumen, atmospheric residues, vacuum gas oils, demetalized oils, naphtha streams, other hydrocarbon streams, or combinations of these materials.

The mixture comprising the greater boiling point fraction stream 106 and the first catalyst 124 is introduced to the first cracking reaction zone 122. The mixture of the greater boiling point fraction stream 106 and first catalyst 124 may be introduced to a top portion of the first cracking reaction zone 122. In one or more embodiments, the first cracking reaction zone 122 may be a downflow reactor or "downer" reactor in which the reactants flow from the first catalyst/feed mixing zone 128 downward through the first cracking reaction zone 122 to the first separation zone 130. Steam 127 may be introduced to the top portion of the first cracking reaction zone 122 to provide additional heating to the mixture of the greater boiling point fraction stream 106 and the first catalyst 124. The greater boiling point fraction stream 106 is reacted by contact with the first catalyst 124 in the first cracking reaction zone 122, which causes at least a portion of the greater boiling point fraction stream 106 to undergo one or more cracking reactions to form one or more cracking reaction products, which may include one or more of the petrochemical products previously described. The first catalyst 124, which has a temperature equal to or greater than the reaction temperature of the first cracking reaction zone 122, may transfer heat to the greater boiling point fraction stream 106 to promote the endothermic cracking reaction.

It should be understood that the first cracking reaction zone 122 of the first FCC unit 120 depicted in FIG. 3 is a simplified schematic of one particular embodiment of the first cracking reaction zone 122 of an FCC unit, and other configurations of the first cracking reaction zone 122 may be suitable for incorporation into the hydrocarbon feed conversion system 100. For example, in some embodiments, the first cracking reaction zone 122 may be an up-flow cracking reaction zone. Other cracking reaction zone configurations are contemplated. In the first cracking reaction zone 122 of the first FCC unit 120, the fluidized first catalyst 124 contacts the greater boiling point fraction stream 106 at high severity conditions. The reaction temperature of the first cracking reaction zone 122 may be from 500° C. to 800° C., from 500° C. to 700° C., from 500° C. to 650° C., from 500° C. to 600° C., from 550° C. to 800° C., from 550° C. to 700° C., from 550° C. to 650° C., from 550° C. to 600° C., from 600° C. to 800° C., from 600° C. to 700° C., or from 600° C. to 650° C. In one or more embodiments, the reaction temperature of the first cracking reaction zone 122 may be from 500° C. to 700° C. In one or more embodiments, the reaction temperature of the first cracking reaction zone 122 may be from 550° C. to 630° C.

A weight ratio of the first catalyst 124 to the greater boiling point fraction stream 106 in the first cracking reaction zone 122 may be from 3:1 to 40:1, from 3:1 to 35:1, from 3:1 to 30:1, from 3:1 to 25:1, from 3:1 to 15:1, from 3:1 to 10:1, from 5:1 to 40:1, from 5:1 to 35:1, from 5:1 to 30:1, from 5:1 to 25:1, from 5:1 to 15:1, from 5:1 to 10:1, from 10:1 to 40:1, from 10:1 to 35:1, from 10:1 to 30:1, from 10:1 to 25:1, from 10:1 to 15:1, from 15:1 to 40:1, from 15:1 to 35:1, from 15:1 to 30:1, from 15:1 to 25:1, from 25:1 to 40:1, from 25:1 to 35:1, from 25:1 to 30:1, or from 30:1 to 40:1. The residence time of the mixture of first catalyst 124 and the greater boiling point fraction stream 106 in the first cracking reaction zone 122 may be from 0.2 seconds (sec) to 3 sec, from 0.2 sec to 2.5 sec, from 0.2 sec to 2 sec, from 0.2 sec to 1.5 sec, from 0.4 sec to 3 sec, from 0.4 sec to 2.5 sec, or from 0.4 sec to 2 sec, from 0.4 sec to 1.5 sec, from 1.5 sec to 3 sec, from 1.5 sec to 2.5 sec, from 1.5 sec to 2 sec, or from 2 sec to 3 sec.

The first catalyst 124 may include one or more of a variety of fluid catalytic cracking catalysts, which may be suitable for use in the first cracking reaction zone 122 operated at high severity conditions. In the first cracking reaction zone 122 of the first FCC unit 120, the first catalyst 124 may be primarily used as a heat carrier to provide heat to the greater boiling point fraction stream 106 to raise the temperature of the greater boiling point fraction stream 106 to the reaction temperature of the first cracking reaction zone 122. Suitable heat carrier materials may include one or more solid materials, such as sand for example, one or more low-activity FCC catalysts, one or more deactivated FCC catalysts, or combinations of these. As used in this disclosure, a low activity FCC catalyst refers to a catalyst having a lesser surface area per unit of weight compared to a high activity FCC catalyst. In one or more embodiments, the first catalyst 124 may include sand. In one or more embodiments, the first catalyst 124 may include a deactivated FCC catalyst.

In one or more embodiments, the first catalyst 124 may include, without limitation, one or more of zeolites, silica-alumina catalysts, carbon monoxide burning promoter additives, bottoms cracking additives, light olefin-producing additives, other catalyst additives, or combinations of these components. Zeolites that may be used in at least a portion of the first catalyst 124 may include, but are not limited to Y, REY, USY, RE-USY zeolites, or combinations of these. The first catalyst 124 may also include a shaped selective catalyst additive, such as ZSM-5 zeolite crystal or other pentasil-type catalyst structures, which are often used in other FCC processes to produce light olefins and/or increase FCC gasoline octane. In one or more embodiments, the first catalyst 124 may include a mixture of a ZSM-5 zeolite crystal and the cracking catalyst zeolite and matrix structure of a conventional FCC cracking catalyst. In one or more embodiments, the first catalyst 124 may be a mixture of Y and ZSM-5 zeolite catalysts embedded with clay, alumina, and binder.

Following the cracking reaction in the first cracking reaction zone 122, the contents of the first cracking reaction zone 122 include the spent first catalyst 125 and the first cracking reaction product stream 126, which may then be passed to the first separation zone 130. In the first separation zone 130, the spent first catalyst 125 is separated from at least a portion of the first cracking reaction product stream 126. In one or more embodiments, the first separation zone 130 may include one or more gas solid separators, such as one or more cyclones. The spent first catalyst 125 exiting from the first separation zone 130 may retain at least a portion of the first cracking reaction product stream 126.

Following separation from the first cracking reaction product stream 126 in the first separation zone 130, the spent first catalyst 125, which may include at least a portion of the first cracking reaction product 126 retained in the spent first catalyst 125, may be passed to the first stripping zone 132, where additional portions of the first cracking reaction product stream 126 are stripped from the spent first catalyst 125 and recovered as a first stripped product stream 134. The first stripped product stream 134 may be passed to one or more downstream unit operations or combined with one or more other streams for further processing. Steam 133 may be introduced to the stripping zone 132 to facilitate stripping the first cracking reaction product 126 from the spent first catalyst 125. The first stripped product stream 134, which may include at least a portion of the steam 133 introduced to the first stripping zone 132, may be discharged from the first stripping zone 132, at which point first stripped product stream 134 may pass through cyclone separators (not shown) and out of the stripper vessel (not shown). The first stripped product stream 134 may be directed to one or more product recovery systems in accordance with known methods in the art. The first stripped product stream 134 may also be combined with one or more other streams, such as the first cracking reaction product stream 126, for example. Combination with other streams is contemplated. The spent first catalyst 125, after having been stripped of at least a portion of first cracking reaction product stream 126 remaining in the spent first catalyst 125, is then passed to the first regeneration zone 162 of the regenerator 160. Operation of the regenerator 160 will be subsequently described in more detail in this disclosure.

Referring to FIG. 3, the lesser boiling point fraction stream 108 is passed from the feed separator 104 (FIG. 2) to the second FCC unit 140. The second FCC unit 140 may include a second catalyst/feed mixing zone 148, the second cracking reaction zone 142, a second separation zone 150, and a second stripping zone 152. The lesser boiling point fraction stream 108 may be introduced to the second catalyst/feed mixing zone 148, where the lesser boiling point fraction stream 108 may be mixed with the second catalyst 144. During steady state operation of the hydrocarbon feed conversion system 100, the second catalyst 144 includes regenerated second catalyst 143 that is passed to the second catalyst/feed mixing zone 148 from one or more second catalyst hoppers 176. The second catalyst hopper 176 receives the regenerated second catalyst 143 from the regenerator 160 following regeneration of the spent second catalyst 145. At initial start-up of the hydrocarbon feed conversion system 100, the second catalyst 144 may include fresh second catalyst (not shown), which is second catalyst that has not been circulated through the second FCC unit 140 and the regenerator 160. In embodiments, fresh second catalyst may also be introduced to second catalyst hopper 176 during operation of the hydrocarbon feed conversion system 100 so that the second catalyst 144 introduced to the second catalyst/feed mixing zone 148 comprises a mixture of fresh second catalyst and regenerated second catalyst 143. Fresh second catalyst may be introduced to the second catalyst hopper 176 periodically during operation to replenish lost second catalyst 144 or compensate for spent second catalyst 145 that becomes permanently deactivated, such as through heavy metal accumulation in the catalyst.

In one or more embodiments, one or more supplemental feed streams (not shown) may be combined with the lesser boiling point fraction stream 108 before introduction of the lesser boiling point fraction stream 108 to the second catalyst/feed mixing zone 148. In other embodiments, one or more supplemental feed streams may be added directly to the second catalyst/feed mixing zone 148, where the supplemental feed stream may be mixed with the lesser boiling point fraction stream 108 and the second catalyst 144 prior to introduction into the second cracking reaction zone 142. The supplemental feed stream may include one or more naphtha streams or other lesser boiling hydrocarbon streams.

The mixture comprising the lesser boiling point fraction stream 108 and the second catalyst 144 is introduced to the second cracking reaction zone 142. The mixture of the lesser boiling point fraction stream 108 and second catalyst 144 may be introduced to a top portion of the second cracking reaction zone 142. In one or more embodiments, the second cracking reaction zone 142 may be a downflow reactor or "downer" reactor in which the reactants flow from the second catalyst/feed mixing zone 148 downward through the second cracking reaction zone 142 to the second separation zone 150. Steam 127 may be introduced to the top portion of the second cracking reaction zone 142 to provide additional heating to the mixture of the lesser boiling point fraction stream 108 and the second catalyst 144. The lesser boiling point fraction stream 108 is reacted by contact with the second catalyst 144 in the second cracking reaction zone 142, which causes at least a portion of the lesser boiling point fraction stream 108 to undergo one or more cracking reactions to form one or more cracking reaction products, which may include one or more of the petrochemical products previously described. The second catalyst 144, which has a temperature equal to or greater than the reaction temperature of the second cracking reaction zone 142, may transfer heat to the lesser boiling point fraction stream 108 to promote the endothermic cracking reaction.

It should be understood that the second cracking reaction zone 142 of the second FCC unit 140 depicted in FIG. 3 is a simplified schematic of one particular embodiment of the second cracking reaction zone 142, and other configurations of the second cracking reaction zone 142 may be suitable for incorporation into the hydrocarbon feed conversion system 100. For example, in some embodiments, the second cracking reaction zone 142 may be an up-flow cracking reaction zone. Other cracking reaction zone configurations are contemplated. In the second cracking reaction zone 142 of the second FCC unit 140, the fluidized second catalyst 144 contacts the lesser boiling point fraction stream 108 at high severity conditions. A reaction temperature of the second cracking reaction zone 142 may be from 500° C. to 800° C., from 500° C. to 700° C., from 500° C. to 650° C., from 500° C. to 600° C., from 550° C. to 800° C., from 550° C. to 700° C., from 550° C. to 650° C., from 550° C. to 600° C., from 600° C. to 800° C., from 600° C. to 700° C., or from 600° C. to 650° C. In some embodiments, the reaction temperature of the second cracking reaction zone 142 may be from 500° C. to 700° C. In other embodiments, the reaction temperature of the second cracking reaction zone 142 may be from 550° C. to 630° C.

A weight ratio of the second catalyst 144 to the lesser boiling point fraction stream 108 in the second cracking reaction zone 142 may be from 3:1 to 40:1, from 3:1 to 35:1, from 3:1 to 30:1, from 3:1 to 25:1, from 3:1 to 15:1, from 3:1 to 10:1, from 5:1 to 40:1, from 5:1 to 35:1, from 5:1 to 30:1, from 5:1 to 25:1, from 5:1 to 15:1, from 5:1 to 10:1, from 10:1 to 40:1, from 10:1 to 35:1, from 10:1 to 30:1, from 10:1 to 25:1, from 10:1 to 15:1, from 15:1 to 40:1, from 15:1 to 35:1, from 15:1 to 30:1, from 15:1 to 25:1, from 25:1 to 40:1, from 25:1 to 35:1, from 25:1 to 30:1, or from 30:1 to 40:1. The residence time of the mixture of second catalyst 144 and the lesser boiling point fraction stream 108 in the second cracking reaction zone 142 may be from 0.2 seconds (sec) to 3 sec, from 0.2 sec to 2.5 sec, from 0.2 sec to 2 sec, from 0.2 sec to 1.5 sec, from 0.4 sec to 3 sec, from 0.4 sec to 2.5 sec, or from 0.4 sec to 2 sec, from 0.4 sec to 1.5 sec, from 1.5 sec to 3 sec, from 1.5 sec to 2.5 sec, from 1.5 sec to 2 sec, or from 2 sec to 3 sec.

The second catalyst 144 may include one or more fluid catalytic cracking catalysts that are suitable for use in the second cracking reaction zone 142 operated at high severity conditions. Examples of fluid catalytic cracking catalysts suitable for use in the second catalyst 144 of the second cracking reaction zone 142 of the second FCC unit 140 may include, without limitation, zeolites, silica-alumina catalysts, carbon monoxide burning promoter additives, bottoms cracking additives, light olefin-producing additives, other catalyst additives, or combinations of these components. Zeolites that may be used as at least a portion of the second catalyst 144 for cracking may include, but are not limited to Y, REY, USY, RE-USY zeolites, or combinations of these. The second catalyst 144 may also include a shaped selective catalyst additive, such as ZSM-5 zeolite crystal or other pentasil-type catalyst structures, which are often used in other FCC processes to produce light olefins and/or increase FCC gasoline octane. In one or more embodiments, the second catalyst 144 may include a mixture of a ZSM-5 zeolite crystal and the cracking catalyst zeolite and matrix structure of a conventional FCC cracking catalyst. In one or more embodiments, the second catalyst 144 may have a weight fraction of ZSM-5 zeolite crystal that is greater than a weight fraction of ZSM-5 zeolite crystal in the first catalyst 124. In one or more embodiments, the second catalyst 144 may be a mixture of Y and ZSM-5 zeolite catalysts embedded with clay, alumina, and binder.

In one or more embodiments, at least a portion of the second catalyst 144 may be modified to include one or more rare earth elements (15 elements of the Lanthanide series of the IUPAC Periodic Table plus scandium and yttrium), alkaline earth metals (Group 2 of the IUPAC Periodic Table), transition metals, phosphorus, fluorine, or any combination of these, which may enhance olefin yield in the second cracking reaction zone 142. Transition metals may include "an element whose atom has a partially filled d sub-shell, or which can give rise to cations with an incomplete d sub-shell" [IUPAC, Compendium of Chemical Terminology, 2nd ed. (the "Gold Book") (1997). Online corrected version: (2006—) "transition element"]. One or more transition metals or metal oxides may also be impregnated onto the catalyst. Metals or metal oxides may include one or more metals from Groups 6-10 of the IUPAC Periodic Table. In some embodiments, the metals or metal oxides may include one or more of molybdenum, rhenium, tungsten, or any combination of these. In one or more embodiments, a portion of the second catalyst 144 may be impregnated with tungsten oxide.

Following the cracking reaction in the second cracking reaction zone 142, the contents of the second cracking reaction zone 142 include spent second catalyst 145 and the second cracking reaction product stream 146, which is passed to the second separation zone 150. In the second separation zone 150, the spent second catalyst 145 is separated from at least a portion of the second cracking reaction product stream 146. In one or more embodiments, the second separation zone 150 may include one or more gas solid separators, such as one or more cyclones. The spent second catalyst 145 exiting from the second separation zone 150 may retain at least a portion of the second cracking reaction product stream 146.

Following separation from the second cracking reaction product stream 146 in the second separation zone 150, the spent second catalyst 145, which may include at least a portion of the second cracking reaction product 146 retained in the spent second catalyst 145, may be passed to the second stripping zone 152, where additional portions of the second cracking reaction product stream 146 are stripped from the spent second catalyst 145 and recovered as a second stripped product stream 154. The second stripped product stream 154 may be passed to one or more downstream unit operations or combined with one or more other streams for further processing. Steam 133 may be introduced to the second stripping zone 152 to facilitate stripping the second cracking reaction product 146 from the spent second catalyst 145. The second stripped product stream 154, which may include at least a portion of the steam 133 introduced to the second stripping zone 152, may be passed out of the second stripping zone 152, at which point the second stripped product stream 154 may pass through cyclone separators (not shown) and out of the stripper vessel (not shown). The second stripped product stream 154 may be directed to one or more product recovery systems in accordance with known methods in the art. The second stripped product stream 154 may also be combined with one or more other streams, such as the second cracking reaction product stream 146. Combination with other streams is contemplated. The spent second catalyst 145, after having been stripped of at least the additional portion of second cracking reaction product stream 146 remaining in the spent second catalyst 145, may then be passed to the second regeneration zone 164 of the regenerator 160. Operation of the regenerator 160 will be subsequently described in more detail in this disclosure.

In some embodiments, the first FCC unit 120 and the second FCC unit 140 share the regenerator 160. The regenerator 160 is a two-zone regenerator that includes the first regeneration zone 162 and the second regeneration zone 164. The spent first catalyst 125 is regenerated in the first regeneration zone 162 to produce regenerated first catalyst 124, and the spent second catalyst 145 is regenerated in the second regeneration zone 162 to produce the regenerated second catalyst 144. In some embodiments, the first regeneration zone 162 may be disposed in a lower portion of the regenerator 160 and the second regeneration zone 164 may be disposed in an upper portion of the regenerator 160. Alternatively, in other embodiments, the regenerator 160 may comprise a first regenerator having the first regeneration zone 162 and a second regenerator separate from the first regenerator and having the second regeneration zone 164.

The regenerator 160 may include a first riser 166 and a second riser 168. The first riser 166 may be positioned between the first stripping zone 132 and the first regeneration zone 162. The spent first catalyst 125 and combustion gas 170 may be introduced to a bottom end of the first riser 166. The combustion gases 170 may include one or more of combustion air, oxygen, fuel gas, fuel oil, other component, or any combinations of these. The combustion gases 170 may convey the spent first catalyst 125 upwards through the first riser 166 to the first regeneration zone 162. The coke deposited on the spent first catalyst 125 in the first cracking reaction zone 122 may begin to oxidize in the presence of the combustion gases 170 in the first riser 166 on the way upward to the first regeneration zone 162. The second riser 168 may be positioned between the second stripping zone 152 and the second regeneration zone 164. The spent second catalyst 145 and combustion gas 170 may be introduced to a bottom end of the second riser 168. The combustion gases 170 may convey the spent second catalyst 145 upwards through the second riser 168 to the second regeneration zone 164. The coke deposited on the spent second catalyst 145 in the second cracking reaction zone 142 may begin to oxidize in the presence of the combustion gases 170 in the second riser 168 on the way upward to the second regeneration zone 164.

The first regeneration zone 162 is separated from the second regeneration zone 164 so that the spent first catalyst 125 and the spent second catalyst 145 are prevented from mixing during the regeneration process. The spent first catalyst 125 is prevented from passing from the first regeneration zone 162 to the second regeneration zone 164, and the spent second catalyst 164 is prevented from passing from the second regeneration zone 164 to the first regeneration zone 162. In one or more embodiments, the regenerator 160 may include the porous separating zone 178 (FIG. 2) positioned between the first regeneration zone 162 and the second regeneration zone 164. The porous separating zone 178 may prevent the passage of the spent first catalyst 125 from the first regeneration zone 162 to the second regeneration zone 164 and prevent passage of the spent second catalyst 145 from the second regeneration zone 164 to the first regeneration zone 162. The porous separating zone 178 may allow flue gas and other gases to pass from the first regeneration zone 162 to the second regeneration zone 164, and vice versa, while maintaining the spent first catalyst 125 in the first regeneration zone 162 and the spent second catalyst 145 in the second regeneration zone 164. In some embodiments, the porous separating zone 178 includes a particulate barrier that prevents solid catalyst particles from passing between the first regeneration zone 162 and the second regeneration zone 164 while allowing gaseous compounds to flow through. In some embodiments, the porous separating zone 178 includes a porous mesh (not shown) positioned between the first regeneration zone 162 and the second regeneration zone 164. The porous mesh of the porous separating zone 178 allows gaseous compounds to flow through the porous mesh but prevents the solid catalyst particles of the spent first catalyst 125 and the second spent catalyst 145 from passing through the porous mesh.

The first regeneration zone 162 may be in fluid communication with the second regeneration zone 164, through the porous separating zone 178 or through another flue gas conduit, so that flue gas from the first regeneration zone 162 may flow to the second regeneration zone 164. The flue gas, which may comprise a mixture of one or more combustion products and unconsumed combustion gases 170, may flow from the first regeneration zone 162, to the second regeneration zone 164, out of the second regeneration zone 164, and out of the regenerator 160 as flue gas stream 172.

The hydrocarbon feed conversion system 100 may include a first catalyst hopper 174 disposed between the first regeneration zone 162 of the regenerator 160 and the first FCC unit 120 and a second catalyst hopper 176 positioned between the second regeneration zone 164 of the regenerator 160 and the second FCC unit 140. The regenerated first catalyst 123 passes from the first regeneration zone 162 to the first catalyst hopper 174, where the regenerated first catalyst 123 accumulates prior to passing from the first catalyst hopper 174 to the first FCC unit 120. The regenerated second catalyst 144 passes from the second regeneration zone 164 to the second catalyst hopper 176, where the regenerated second catalyst 144 accumulates prior to passing from the second catalyst hopper 176 to the second FCC unit 140.

The first catalyst 124 is continuously circulated through the first FCC unit 120, the first regeneration zone 162 of the regenerator 160, and the first catalyst hopper 174. Coke deposits form on the first catalyst 124 in the first cracking reaction zone 122 resulting in the spent first catalyst 125. Additionally, the spent first catalyst 125 may absorb or retain small portions of the greater boiling point fraction stream 106, the first cracking reaction product stream 126, or both, which may not be completely stripped from the spent first catalyst 125. As previously described, upon exiting the first cracking reaction zone 122, the spent first catalyst 125 is separated from the first cracking reaction product stream 126 in the first separating zone 130 and stripped of a portion of the first cracking reaction product stream 126 or greater boiling point fraction stream 106 remaining in the spent first catalyst 125. The spent first catalyst 125 is then mixed with combustion air 170 and passed to the first regeneration zone 162, where coke deposits and residual reactants and reaction products are at least partially oxidized (combusted). The coke on the spent first catalyst 125 may be partially oxidized to carbon monoxide in the first regeneration zone 162 according to the following chemical equation (1):

$$C + \tfrac{1}{2} O_2 \rightarrow CO \qquad \text{Equation (1)}$$

Partial oxidation of the coke deposits in the first regeneration zone 162 may help to maintain a combustion temperature in the first regeneration zone 162 that is less than a failure temperature of the construction materials used for the regenerator 160. At least a portion of the coke deposits on the spent first catalyst 125 may additionally be fully oxidized to carbon dioxide in the first regeneration zone 162. The composition and flow rate of the combustion gas 170 may be adjusted to limit full oxidation of the coke deposits on the spent first catalyst 125.

The regenerated first catalyst 123, which is at an elevated temperature, is then passed to the first catalyst hopper 174, and from there, recycled back to the first catalyst/feed mixing zone 128 as the first catalyst 124 to be combined with the greater boiling point fraction stream 106. The temperature of the regenerated first catalyst 123, after regeneration in the first regeneration zone 162, may be equal to or greater than the reaction temperature in the first cracking reaction zone 122 of the first FCC unit 120. The greater temperature of the regenerated first catalyst 123 provides heat for the endothermic cracking reaction in the first cracking reaction zone 122. The regenerated first catalyst 123 passing out of the first regeneration zone 162 may contain small amounts of residual coke deposits and other contaminants.

The regenerated first catalyst 123 passing out of the first regeneration zone 162 may have less than 1 wt. % coke deposits, based on the total weight of the regenerated first catalyst 123. In some embodiments, the regenerated first catalyst 123 exiting the first regeneration zone 162 may have less than 0.5 wt. %, less than 0.1 wt. %, or less than 0.05 wt. % coke deposits. In some embodiments, the regenerated first catalyst 123 passed from the first regeneration zone 162 to the first catalyst hopper 174 may have from 0.001 wt. % to 1 wt. %, from 0.001 wt. % to 0.5 wt. %, from 0.001 wt. % to 0.1 wt. %, from 0.001 wt. % to 0.05 wt. %, from 0.005 wt. % to 1 wt. %, from 0.005 wt. % to 0.5 wt. %, from 0.005 wt. % to 0.1 wt. %, from 0.005 wt. % to 0.05 wt. %, from 0.01 wt. % to 1 wt. %, from 0.01 wt. % to 0.5 wt. % to 0.01 wt. % to 0.1 wt. %, from 0.01 wt. % to 0.05 wt. % coke deposits, based on the total weight of the regenerated first catalyst 123. In one or more embodiments, the regenerated first catalyst 123 leaving the first regeneration zone 162 may be substantially free of coke deposits. As used in this disclosure, the term "substantially free" of a component means less than 1 wt. % of that component in a particular portion of a catalyst, stream, or reaction zone. As an example, the regenerated first catalyst 123, which is substantially free of coke deposits, may have less than 1 wt. % of coke deposits.

The second catalyst 144 is continuously circulated through the second FCC unit 140, the second regeneration zone 164 of the regenerator 160, and the second catalyst hopper 176. Coke deposits form on the second catalyst 144 in the second cracking reaction zone 142 resulting in the spent second catalyst 145. Additionally, the spent second catalyst 145 may absorb or retain small portions of the lesser boiling point fraction stream 108, the second cracking reaction product stream 146, or both, which may not be completely stripped from the spent second catalyst 145 in the second stripping zone 152. As previously described, upon exiting the second cracking reaction zone 142, the spent second catalyst 145 may be separated from the second cracking reaction product stream 146 in the second separating zone 150 and may be stripped of at least a portion of the second cracking reaction product stream 146 or lesser boiling point fraction stream 108 remaining in the spent second catalyst 145. The spent second catalyst 145 may then be mixed with combustion air 170 and passed to the second regeneration zone 164, where coke deposits and any residual reactants (lesser boiling point fraction stream 108) and reaction products (second cracking reaction product 146) are oxidized. A portion of the coke deposits on the spent second catalyst 145 may be fully oxidized to carbon dioxide in the first regeneration zone 162 according to the following chemical equation (2):

$$C + O_2 \rightarrow CO_2 \quad \text{Equation (2)}$$

At least another portion of the coke deposits in the spent second catalyst 145 may be partially oxidized to carbon monoxide according Equation 1. Due to the lesser concentration of coke producing compounds in the lesser boiling point fraction stream 108, lesser coke levels may be formed on the spent second catalyst 145 discharged from the second cracking reaction zone 142 as compared to the greater coke deposits on the spent first catalyst 125 discharged from the first cracking reaction zone 122. An efficiency of the second cracking reaction zone 142 may be adversely impacted by the lesser coke levels deposited on the spent second catalyst 145. Lesser coke levels on the spent second catalyst 145 may result in less heat generated by the regeneration process in the second regeneration zone 164, which may result in a temperature of the regenerated second catalyst 143 leaving the second regeneration zone 164 that is less than a reaction temperature of the second cracking reaction zone 142. Decreasing the reaction temperature in the second cracking reaction zone 142 because of the lesser temperature of the regenerated second catalyst 143 passed to the second cracking reaction zone 142 may greatly reduce the yield of the greater value petrochemical products by the second cracking reaction zone 142.

To compensate for the reduced heat generation caused by the lesser coke levels in the spent second catalyst 145, and thus the lesser temperature of the regenerated second catalyst 143 discharged from the second regeneration zone 164, the hot flue gas from the first regeneration zone 162 may be passed to the second regeneration zone 164 where the hot flue gas may be contacted with the spent second catalyst 145 in the second regeneration zone 164. The hot flue gas may transfer heat to the spent second catalyst 145, thus, raising the discharge temperature of the regenerated second catalyst 143. Additional heat may be generated in the second regeneration zone 164 by further oxidizing carbon monoxide in the flue gas coming from the first regeneration zone 162 into carbon dioxide, according to the following Equation 3:

$$CO + \tfrac{1}{2}O_2 \rightarrow CO_2 \quad \text{Equation (3)}$$

Thus, the greater amounts of coke deposits on the spent first catalyst 125, which result from cracking of the greater boiling point fraction stream 106 in the first cracking reaction zone 122, may heat balance the hydrocarbon feed conversion system 100 by providing additional heat to the regenerated second catalyst 143 in the second regeneration zone 164 to compensate for the lesser amounts of coke deposits formed on the spent second catalyst 145 in the second cracking reaction zone 142. Using the greater coke levels in the spent first catalyst 125 to generate additional heat to raise the temperature of the regenerated second catalyst 143 may avoid the need to add additional fuel gases to the combustion gases to raise the temperature of the regenerated second catalyst 143 through fuel gas combustion.

The composition and flow rate of the combustion gas 170 into the second regeneration zone 164 may be adjusted to control oxidation of the coke deposits on the spent second catalyst 125 and oxidation of carbon monoxide in the flue gas to carbon dioxide. The flue gas 172 may then be discharged from the second regeneration zone 164. The flue gas 172 may be passed to one or more operations for further treatment, such as heat recovery or further oxidation, for example.

The regenerated second catalyst 143, which is at an elevated temperature is then passed to the second catalyst hopper 176, and from there, recycled back to the second FCC unit 140 as the second catalyst 144. The temperature of the regenerated second catalyst 143 after regeneration in the second regeneration zone 164 may be equal to or greater than the reaction temperature in the second cracking reaction zone 142 of the second FCC unit 140. The greater temperature of the regenerated second catalyst 143 in the second catalyst hopper 176 and passed to the second cracking reaction zone 142 may provide heat for the endothermic cracking reaction in the second cracking reaction zone 142.

The regenerated second catalyst 143 passing out of the second regeneration zone 164 may contain small amounts of residual coke deposits and other contaminants. The regenerated second catalyst 143 passing out of the first regeneration zone 162 may have less than 1 wt. %, less than 0.5 wt. %, less than 0.1 wt. %, or less than 0.05 wt. % coke deposits, based on the total weight of the regenerated second catalyst 143. In some embodiments, the regenerated second catalyst 143 exiting the second regeneration zone 164 may have less than 0.05 wt. % coke deposits. In some embodiments, the regenerated second catalyst 143 passed from the second regeneration zone 164 to the second catalyst hopper 176 may have from 0.001 wt. % to 1 wt. %, from 0.001 wt. % to 0.5 wt. %, from 0.001 wt. % to 0.1 wt. %, from 0.001 wt. % to 0.05 wt. %, from 0.005 wt. % to 1 wt. %, from 0.005 wt. % to 0.5 wt. %, from 0.005 wt. % to 0.1 wt. %, from 0.005 wt. % to 0.05 wt. %, from 0.01 wt. % to 1 wt. %, from 0.01 wt. % to 0.5 wt. % to 0.01 wt. % to 0.1 wt. %, from 0.01 wt. % to 0.05 wt. % coke deposits, based on the total weight of the regenerated second catalyst 143. In other embodiments, the regenerated second catalyst 143 may be substantially free of coke deposits.

The dual-zone catalyst regenerator 160 may enable a crude oil feed stream to be converted into greater value petrochemical products, such as ethane, propene, butenes, gasoline, other olefins, or combinations of these, in a dual downflow HSFCC system with greater efficiency. The dual-zone catalyst regenerator 160 having the first regeneration zone 162 and the second regeneration zone 164 may allow different catalysts to be used in the first cracking reaction zone 122 and the second cracking reaction zone 142, which may improve the efficiency of each reaction zone. Additionally, operation of the dual-zone catalyst regenerator 160 may enable independent control of the temperature of the first catalyst 124 and the temperature of the second catalyst 144, which may allow independent temperature control of the first cracking reaction zone 122 and the second cracking reaction zone 142 without employing one or more additional heat transfer operations with the regenerator 160 and the first and second FCC units 120, 140. For example, in some embodiments, the first cracking reaction zone 122 may be operated at a first temperature, and the second cracking reaction zone 142 may be simultaneously operated at a second temperature that is different than the first temperature. In embodiments, the first temperature may be from 500° C. to 600° C., and the second temperatures may be from 600° C. to 700° C.

The first cracking reaction product stream 126 and the second cracking reaction product stream 146 may each contain at least one greater value petrochemical product such as ethane, propene, butenes, other olefins, gasolines, or combinations of these. Referring to FIG. 2, the first cracking reaction product stream 126 leaving the first separation zone 130 and the second cracking reaction product stream 146 leaving the second separation zone 150 may be combined into a combined cracking product stream 114. In one or more embodiments, the first stripped product stream 134 (FIG. 3), the second stripped product stream 154 (FIG. 3), or both may be combined into the combined cracking product stream 114. The combined cracking product stream 114 may be separated by one or more product stream separators 112 into one or more system product streams 110. For example, the product stream separator 112 may be a distillation column which separates the combined cracking product stream 114 (one or both of the first cracking reaction product stream 126 and the second cracking reaction product stream 146 may be individually passed to the product stream separator 112 rather than being combined) into one or more system product streams 110, which may include one or more fuel oil streams, gasoline streams, mixed butenes stream, butadiene stream, propene stream, ethylene stream, methane stream, or combinations of these. Each system product stream 110 may be passed to one or more additional unit operations for further processing. In one or more embodiments, the first cracking reaction product stream 126 and the second cracking reaction product stream 146 may be individually introduced to the product stream separator 112. As used in this disclosure, the one or more system product streams 110 may be referred to as petrochemical products, which may be used as intermediates in downstream chemical processing or packaged as finished products. The product stream separator 112 may also produce one or more recycle streams 111, which may be recycled back to the first FCC unit 120, second FCC unit 140, or both the first FCC unit 120 and the second FCC unit 140.

A process for producing petrochemical products from a hydrocarbon material will now be described. The process for producing olefins from a hydrocarbon material comprises separating the hydrocarbon material into a lesser boiling point fraction and a greater boiling point fraction, cracking at least a portion of the greater boiling point fraction in the presence of a first catalyst 124 at a reaction temperature of from 500° C. to 700° C. to produce a first cracking reaction product and a spent first catalyst 125, and cracking at least a portion of the lesser boiling point fraction in the presence of a second catalyst 144 at a reaction temperature of from 500° C. to 700° C. to produce a second cracking reaction product and a spent second catalyst 145. The process further comprises separating at least a portion of the first cracking reaction product from the spent first catalyst 125 and separating at least a portion of the second cracking reaction product from the spent second catalyst 145. The process comprises regenerating at least a portion of the spent first catalyst 125 to produce a regenerated first catalyst 123, maintaining the spent second catalyst 145 separate from the spent first catalyst 125, passing heat from regeneration of the spent first catalyst 125 to the spent second catalyst 145, and regenerating at least a portion of the spent second catalyst 145 to produce a regenerated second catalyst 143. The process comprises recovering the first cracking reaction product and the second cracking reaction product.

In some embodiments, the process comprises contacting the spent second catalyst 145 with a flue gas from regeneration of the first spent catalyst 125. In embodiments, the first catalyst 124 may be different than the second catalyst. The first catalyst 124 may be a sand or a low-activity FCC catalyst. The second catalyst 144 may be a high-activity FCC catalyst. In some embodiments, the hydrocarbon material is crude oil. In some embodiments, the hydrocarbon material may include at least one of a crude oil, vacuum residue, tar sands, bitumen, atmospheric residue, vacuum gas oils, demetalized oils, naphtha, or combinations of these materials. The first cracking reaction product, the second cracking reaction product, or both the first cracking reaction product and the second cracking reaction product may comprise at least one of ethylene, propene, butene, or pentene.

Referring to FIGS. 2 and 3, a process for operating a system, such as the hydrocarbon feed conversion system 100, having a first FCC unit 120 and a second FCC unit 140 for producing petrochemical products from the hydrocarbon feed stream 102 comprises introducing the hydrocarbon feed stream 102 to the feed separator 104, separating the hydrocarbon feed stream 102 into a lesser boiling point fraction 108 and a greater boiling point fraction 106 in the feed separator 104, passing the greater boiling point fraction 106 to the first FCC unit 120, cracking at least a portion of the greater boiling point fraction 106 in the first FCC unit 120 in the presence of a first catalyst 124 and at a reaction temperature of from 500° C. to 700° C. to produce a first cracking reaction product 126 and a spent first catalyst 125, passing the lesser boiling point fraction 108 to the second FCC unit, and cracking at least a portion of the lesser boiling point fraction 108 in the second FCC unit 140 in the presence of a second catalyst 144 and at a reaction temperature of from 500° C. to 700° C. to produce a second cracking reaction product 146 and a spent second catalyst 145. The process further comprises passing the spent first catalyst 125 to a first regeneration zone 162, regenerating at least a portion of the spent first catalyst 125 in the first regeneration zone 162 to produce a regenerated first catalyst 123, passing the spent second catalyst 145 to a second regeneration zone 164 separate from the first regeneration zone 162, and regenerating at least a portion of the spent second catalyst 145 in the second regeneration zone 164 to produce a regenerated second catalyst 143. The process includes transferring heat from the first regeneration zone 162 to the second regeneration zone 164, recycling the regenerated first catalyst 123 back to the first FCC unit 120 and the regenerated second catalyst 143 back to the second FCC unit 142, and recovering the first cracking reaction product 126 and the second cracking reaction product 146.

The hydrocarbon feed stream 102 may comprise a crude oil. In some embodiments, the hydrocarbon feed stream 102 may comprise at least one of a crude oil, vacuum residue, tar sands, bitumen, atmospheric residue, vacuum gas oils, demetalized oils, naphtha streams, or combinations of these materials. The one or more petrochemical products may include one or more fuel oil, gasoline, mixed butenes, butadiene, propene, ethylene, pentene, other olefins, methane, or combinations of these. In some embodiments, the first catalyst 124 may be different than the second catalyst 144. In some embodiments, the first catalyst 124 may be sand or a low-activity FCC catalyst. In some embodiments, the second catalyst 144 is a high activity FCC catalyst. In some embodiments, at least a portion of the second catalyst 144 may comprise a ZSM-5 zeolite catalyst.

The process operating the system for producing one or more petrochemical products from a hydrocarbon feed stream 102 may further comprise mixing the first catalyst 124 and the greater boiling point fraction 106 in a first mixing zone 128 positioned upstream of a first cracking reaction zone 122 of the first FCC unit 120 and mixing the second catalyst 144 with the lesser boiling point fraction 108 in a second mixing zone 148 positioned upstream of the second cracking reaction zone 142 of the second FCC unit 140. In embodiments, the process further comprises separating at least a portion of the first cracking reaction product 126 from the spent first catalyst 125 in a first separating zone 130 before passing the spent first catalyst 125 to the first regeneration zone 162, and separating at least a portion of the second cracking reaction product 146 from the spent second catalyst 145 in a second separating zone 130 before passing the spent second catalyst 145 to the second regeneration zone 164. The first cracking reaction product 126, the second cracking reaction product 146, or both the first cracking reaction product 126 and the second cracking reaction product 146 may comprise one or more of ethylene, propene, butenes, or pentenes. The first cracking reaction product 126, the second cracking reaction product 146, or the first cracking reaction product 126 and the second cracking reaction product 146 may also include other olefins, gasolines, fuel oils, other products, or combinations of products.

The process of operating the system for producing one or more petrochemical products from a hydrocarbon feed stream 102 may further comprise stripping another portion of the first cracking reaction product 126 from the spent first catalyst 125 upstream of the first regeneration zone 162 and stripping another portion of the second cracking reaction product 146 from the spent second catalyst 145 upstream of the second regeneration zone 164. In some embodiments, the process may further comprise stripping a portion of the first cracking reaction product 126 from the spent first catalyst 125 upstream of the first regeneration zone 162 and stripping a portion of the second cracking reaction product 146 from the spent second catalyst 145 upstream of the second regeneration zone 164.

The process of operating the system for producing one or more petrochemical products from a hydrocarbon feed stream 102 may further comprise passing a flue gas stream 172 from the first regeneration zone 162 to the second regeneration zone 164, and contacting the spent second catalyst 145 in the second regeneration zone 164 with the flue gas stream 172 passed from the first regeneration zone 162. For example, in some embodiments, the process may comprise contacting the spent second catalyst 145 with a flue gas passed from the first regeneration zone 162 and received in the second regeneration zone 164. In some embodiments, the process of operating the system may further comprise raising a temperature of the spent second catalyst 145 in the second regeneration zone 164 by contacting the spent second catalyst 145 with a flue gas exhausted from the first regeneration zone 162 to the second regeneration zone 162. In embodiments, the process of operating the system may comprise maintaining the spent first catalyst 125 in the first regeneration zone 162 separate from the spent second catalyst 145 in the second regeneration zone 164. In some embodiments, the process may include restricting the flow of the spent first catalyst 125 from the first regeneration zone 162 to the second regeneration zone 164 and restricting the flow of the spent second catalyst 145 from the second regeneration zone 164 to the first regeneration zone 162. In some embodiments, the first regeneration zone 162 and the second regeneration zone 164 are disposed in a single regenerator 160.

The process of operating the system for producing one or more petrochemical products from a hydrocarbon feed stream 102 may further comprise recycling the regenerated first catalyst 123 back to a first cracking reaction zone 122 of the first FCC unit 120 and recycling the regenerated second catalyst 143 back to a second cracking reaction zone 142 of the second FCC unit 140. In some embodiments, the process may include passing the regenerated first catalyst 123 from the first regeneration zone 162 to a first catalyst feed hopper 174 and passing the regenerated second catalyst 143 from the second regeneration zone 164 to a second catalyst feed hopper 176.

Another process for producing one or more petrochemical products from a hydrocarbon feed stream comprises separating the hydrocarbon feed stream into a lesser boiling point fraction and a greater boiling point fraction, cracking the greater boiling point fraction in a first fluid catalytic cracking (FCC) unit in the presence of a first catalyst and at a reaction temperature of from 500° C. to 700° C. to produce a first cracking reaction product, cracking the lesser boiling point fraction in a second FCC unit in the presence of a second catalyst and at a reaction temperature of from 500° C. to 700° C. to produce a second cracking reaction product, the second FCC unit operated in parallel with the first FCC unit, regenerating the first catalyst in a first regeneration zone, transferring heat from the first regeneration zone to the second regeneration zone, regenerating the second catalyst in a second regeneration zone separate from the first regeneration zone, recycling the first catalyst back to the first FCC unit and the second catalyst back to the second FCC unit, and recovering the first cracking reaction product and the second cracking reaction product.

EXAMPLES

The following examples illustrate one or more additional features of the present disclosure described previously.

Comparative Example 1: Cracking Heavy and Light Fractions Using the Same Catalyst Comparative Example 1 provides an example of a conventional FCC process in which the same catalyst is used to crack both the heavy and light fractions of the crude oil feed stream. A crude oil feed stream was separated into a heavy fraction (greater boiling point fraction) and a light fraction (lesser boiling point fraction) in a fractionator operated at a temperature of 250° C. The crude oil feed stream was Saudi Arabian Extra Light Crude Oil (AXL) provided by Saudi Aramco. Each of the heavy fraction and the light fraction were separately cracked in a laboratory-scale micro downer FCC unit using different operating conditions. A general description of the laboratory-scale micro downer FCC unit and operation of the unit may be found in Corma et al., *A New Continuous Laboratory Reactor For the Study of Catalytic Cracking, Applied Catalysts A: General.* 232(1): 247-263 (June 2002), which is incorporated by reference in this disclosure in its entirety. The heavy fraction was cracked at a cracking reaction temperature of 600° C. and a weight ratio of catalyst to oil (heavy fraction) of 31:1. The light fraction was cracked at a cracking reaction temperature of 640° C. and a weight ratio of catalyst to oil (light fraction) of 22:1. The same catalyst was used as the cracking catalyst for both the heavy fraction and the light fraction. The catalyst was a Y Zeolite catalyst with an additive comprising ZSM-5 Zeolite catalyst. The catalyst included 25 wt. % of the ZSM-5 Zeolite, based on the total weight of the catalyst. Following the separate cracking reactions, the catalyst from each reaction was separately stripped of reaction products at a stripping temperature of 450° C. The reaction product streams from the two cracking reactions were analyzed for total conversion and yields of ethylene, propylene, total $C_4$, gasoline ($C_5$-216° C.), light cycle oil (LCO, 216-343° C.), heavy cycle oil (HCO, >343° C.), and coke yield. The reaction conditions and results of the conversion and yield analysis for Comparative Example 1 are subsequently provided in Table 2.

TABLE 2

Total Conversion and Yield for Comparative Example 1

| Property | Light Fraction (bp < 250° C.) | Heavy Fraction (bp > 250° C.) |
| --- | --- | --- |
| Catalyst to Oil Weight Ratio | 20 | 20 |
| Cracking Reactor Temperature (° C.) | 640 | 600 |
| Total Conversion (wt. %) | 37.7 | 72.5 |
| Ethylene Yield (wt. %) | 3.5 | 3.1 |
| Propene Yield (wt. %) | 8.0 | 16.2 |
| Total C4 (wt. %) | 5.5 | 13.4 |
| Gasoline (C5-216° C.) (wt. %) | 69.7 | 28.2 |
| LCO (216-343° C.) (wt. %) | 8.0 | 23 |
| HCO (>343° C.) (wt. %) | 0.0 | 6.7 |
| Coke Yield (wt. %) | 0.4 | 4.0 |

As shown in Table 2, the conversion and yield for the light fraction of Comparative Example 1 was substantially less than the conversion and yield of the heavy fraction. Since the same catalyst was used in cracking the light fraction and the heavy fraction in Comparative Example 1, the data in Table 2 indicates that cracking the light fraction with the same catalyst used to crack the heavy fraction generally results in reduced conversion of the light fraction and reduced yields of greater value petrochemical products from the light fraction. The data for Comparative Example 1 suggest an opportunity for maximizing the yield of greater value petrochemical products through being able to independently control the first cracking reaction zone for the heavy fraction and the second cracking reaction zone for the light fraction. As will be shown in Example 2, the type of catalyst used to crack the light fraction can have a great influence on the conversion and yield of the cracking reaction for the light fraction.

Example 2: Effects of Different Catalysts on Conversion and Yield for Cracking the Light Fraction Example 2 evaluates the effects on total conversion and propene selectivity of using alternative cracking catalysts to crack the light fraction of the crude oil feed stream. A crude oil feed stream was separated into a heavy fraction (greater boiling point fraction) and a light fraction (lesser boiling point fraction) in a fractionator operated at a temperature of 250° C. The crude oil feed stream was AXL crude oil provided by Saudi Aramco. The light fraction was cracked using four different types of commercially available FCC catalysts in a MAT unit at a cracking reaction temperature of 600° C. and a weight ratio of catalyst to oil (light fraction) of from 3 to 7. Each of the commercially available FCC catalysts was obtained from BASF, Iselin, N.J. and included different compositions or structures. The catalysts of Example 2 were different than the catalyst Comparative Example 1, which was a Y Zeolite catalyst with 25 wt. % ZSM-5 Zeolite catalyst additive based on the total weight of the catalyst. Following the separate cracking reactions, each of the catalysts of Example 2 were stripped of the reaction products at a stripping temperature of 600° C. The reaction products obtained for each of the catalysts were analyzed for overall conversion and propene yield. For each commercial catalyst type of Example 2, the average conversion and average propene yield were calculated from the data. The reaction temperature and catalyst/oil weight ratio for each catalyst evaluated are subsequently provided in Table 3. The results for the overall conversion and propene yield for each of the catalysts of Example 2 are shown in FIG. 4 with the reference number in FIG. 4 for each catalyst provided in Table 3.

TABLE 3

Reaction Temperature and Catalyst to Oil Ratio for the Reactions of Example 2.

Figure 4:
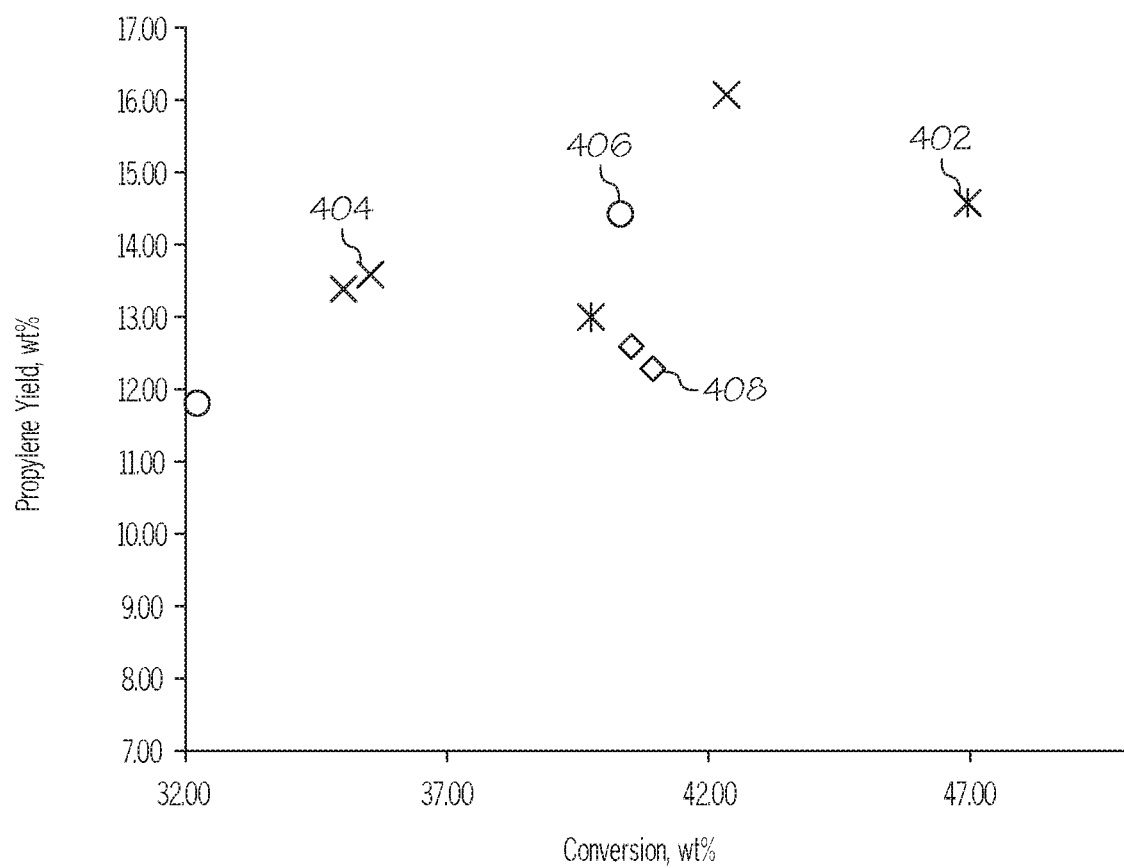
FIG. 4 graphically depicts conversion and propene yields obtained from a HSFCC process operated with different types of commercial FCC catalysts, according to one or more embodiments described in this disclosure.

| | Catalyst A | Catalyst B | Catalyst C | Catalyst D |
| --- | --- | --- | --- | --- |
| Reference No. in FIG. 4 | 402 | 404 | 406 | 408 |
| Reaction Temperature (° C.) | 600 | 600 | 600 | 600 |
| Catalyst/Oil Weight Ratio | 3-7 | 3-7 | 3-7 | 3-7 |

The results for each of the different commercial catalysts are graphically depicted in FIG. 4, which illustrates that the use of different cracking catalysts for cracking the light fraction of a crude oil feed may greatly influence the overall conversion and propene yield of the cracking reaction. As shown in FIG. 4, the overall conversion for cracking the light fraction ranges from 35 wt. % to 47 wt. % and the propene yield ranges from 12 wt. % to 16 wt. % depending on the type of catalyst used at the same reaction conditions. The conversion and propene yield results in FIG. 4 for Example 2 indicate that changing the type of catalyst used to crack the light fraction can increase the conversion and propene yield of the FCC reactor system.

Additionally, comparing cracking of the light fraction in Example 2 to cracking the light fraction in Comparative Example 1 indicates that the overall conversion and propene selectivity of the FCC process can be improved by using a different catalyst to crack the light fraction. For example, one of the reactions performed with Catalyst B of Example 2 resulted in a propene yield of greater than 16.0 wt. % and an overall conversion of greater than 42 wt. %. This is almost three times the propene yield obtained for cracking the light fraction using the cracking catalyst in Comparative Example 1, which was the same catalyst used to crack the heavy fraction. The reactions of Comparative Example 1 were run at a greater cracking temperature and greater catalyst to oil ratio compared to the reactions of Example 2 having different catalyst. Each of the catalysts in Example 2 unexpectedly produced a propene yield of greater than 12 wt. % from cracking the light fraction, which was at least twice the propene yield achieved using the catalyst of Comparative Example 1 to crack the light fraction (lesser boiling point fraction), even though the reactions were run at a lesser cracking temperature and lesser catalyst to oil ratio. Comparison of the propene yields for the catalyst of Example 2 to the propene yield achieved by the catalyst of Comparative Example 1, demonstrates that use of a different catalyst for the light fraction can greatly increase the overall conversion and yield of greater-value petrochemical products, such as ethylene, propene, butenes, and other olefins compared to using the same catalyst for the light fraction that is used for the heavy fraction.

The HSFCC system of this disclosure, specifically the two-stage regenerator 160 having the first regeneration zone 162 and the second regeneration zone 164 separate from one another, enables separate catalysts to be used for the heavy fraction and the light fraction to improve the conversion and yield of greater-value petrochemical products.

A first aspect of the present disclosure is directed to a process for producing petrochemical products from a hydrocarbon material that includes separating the hydrocarbon material into a lesser boiling point fraction and a greater boiling point fraction and cracking at least a portion of the greater boiling point fraction in the presence of a first catalyst at a reaction temperature of from 500° C. to 700° C. to produce a first cracking reaction product and a spent first catalyst. The method further includes cracking at least a portion of the lesser boiling point fraction in the presence of a second catalyst at a reaction temperature of from 500° C. to 700° C. to produce a second cracking reaction product and a spent second catalyst. The method may further include separating at least a portion of the first cracking reaction product from the spent first catalyst, separating at least a portion of the second cracking reaction product from the spent second catalyst, and regenerating at least a portion of the spent first catalyst to produce a regenerated first catalyst. The method may further include maintaining the spent second catalyst separate from the spent first catalyst, transferring heat from regeneration of the spent first catalyst to the spent second catalyst, and regenerating at least a portion of the spent second catalyst to produce a regenerated second catalyst. The method may further include recovering the first cracking reaction product and the second cracking reaction product.

A second aspect of the present disclosure may include the first aspect, further comprising contacting the spent second catalyst with a flue gas from regeneration of the first spent catalyst.

A third aspect of the present disclosure may include either of the first or second aspects, where the first catalyst is different than the second catalyst.

A fourth aspect of the present disclosure may include any of the first through third aspects, where the first catalyst is sand or a low activity FCC catalyst.

A fifth aspect of the present disclosure may include any of the first through fourth aspects, where the second catalyst is a high-activity FCC catalyst.

A sixth aspect of the present disclosure may include any of the first through fifth aspects, where at least a portion of the second catalyst comprises a ZSM-5 zeolite catalyst.

A seventh aspect of the present disclosure may include any of the first through sixth aspects, where the hydrocarbon material comprises crude oil.

An eighth aspect of the present disclosure may include any of the first through sixth aspects, where the hydrocarbon material comprises at least one of a crude oil, vacuum residue, tar sands, bitumen, atmospheric residue, vacuum gas oils, demetalized oils, naphtha, or combinations of these.

A ninth aspect of the present disclosure may include any of the first through eighth aspects, where the first cracking reaction product or the second cracking reaction product comprises at least one of ethylene, propene, butene, or pentene.

A tenth aspect of the present disclosure may include any of the first through ninth aspects, further comprising mixing the regenerated first catalyst with the greater boiling point fraction before cracking the at least a portion of the greater boiling point fraction.

An eleventh aspect of the present disclosure may include any of the first through tenth aspects, further comprising mixing the regenerated second catalyst with the lesser boiling point fraction before cracking the at least a portion of the lesser boiling point fraction.

A twelfth aspect of the present disclosure may include any of the first through ninth aspects, further comprising recycling the regenerated first catalyst back into contact with the greater boiling point fraction, and recycling the regenerated second catalyst back into contact with the lesser boiling point fraction.

A thirteenth aspect of the present disclosure is directed to a process for operating a hydrocarbon feed conversion system having a first fluidic catalytic cracking (FCC) unit and a second FCC unit for producing petrochemical products from a hydrocarbon feed stream, the process comprising introducing the hydrocarbon feed stream to a feed separator, separating the hydrocarbon feed stream into a lesser boiling point fraction and a greater boiling point fraction in the feed separator, passing the greater boiling point fraction to the first FCC unit, and passing the lesser boiling point fraction to the second FCC unit. The process further includes cracking at least a portion of the greater boiling point fraction in first FCC unit in the presence of a first catalyst at a reaction temperature of from 500° C. to 700° C. to produce a first cracking reaction product and a spent first catalyst, and cracking at least a portion of the lesser boiling point fraction in the second FCC unit in the presence of a second catalyst and at a reaction temperature of from 500° C. to 700° C. to produce a second cracking reaction product and a spent second catalyst. The process may further include passing the spent first catalyst to a first regeneration zone, regenerating at least a portion of the spent first catalyst in the first regeneration zone to produce a regenerated first catalyst, passing the spent second catalyst to a second regeneration zone separate from the first regeneration zone, and regenerating at least a portion of the spent second catalyst in the second regeneration zone to produce a regenerated second catalyst. The process further includes transferring heat from the first regeneration zone to the second regeneration zone and recycling the regenerated first catalyst to the first FCC unit and the regenerated second catalyst to the second FCC unit. The process may further include recovering the first cracking reaction product and the second cracking reaction product.

A fourteenth aspect of the present disclosure may include the thirteenth aspect, further comprising passing a flue gas stream from the first regeneration zone to the second regeneration zone, and contacting the spent second catalyst in the second regeneration zone with the flue gas stream.

A fifteenth aspect of the present disclosure may include the thirteenth aspect, further comprising contacting the spent second catalyst with a flue gas exhausted from the first regeneration zone.

A sixteenth aspect of the present disclosure may include any of the thirteenth through fifteenth aspects, further comprising maintaining the spent first catalyst in the first regeneration zone separate from the spent second catalyst in the second regeneration zone.

A seventeenth aspect of the present disclosure may include any of the thirteenth through sixteenth aspects, where the second regeneration zone is separated from the first regeneration zone by a porous separation zone.

An eighteenth aspect of the present disclosure may include any of the thirteenth through fifteenth aspects, further comprising restricting flow of the spent first catalyst from the first regeneration zone to the second regeneration zone, and restricting flow of the spent second catalyst from the second regeneration zone to the first regeneration zone.

A nineteenth aspect of the present disclosure may include any of the thirteenth through eighteenth aspects, where the first regeneration zone and the second regeneration zone are disposed within a single regenerator.

A twentieth aspect of the present disclosure may include any of the thirteenth through nineteenth aspects, where the first catalyst is different than the second catalyst.

A twenty-first aspect of the present disclosure may include any of the thirteenth through twentieth aspects, where the first catalyst is a sand or a low activity FCC catalyst.

A twenty-second aspect of the present disclosure may include any of the thirteenth through twenty-first aspects, where the second catalyst comprises a high-activity FCC catalyst.

A twenty-third aspect of the present disclosure may include any of the thirteenth through twenty-second aspects where at least a portion of the second catalyst comprises a ZSM-5 zeolite catalyst.

A twenty-fourth aspect of the present disclosure may include any of the thirteenth through twenty-third aspects, where the hydrocarbon feed stream comprises crude oil.

A twenty-fifth aspect of the present disclosure may include any of the thirteenth through twenty-third aspects, where the hydrocarbon feed stream comprises at least one of a crude oil, vacuum residue, tar sands, bitumen, atmospheric residue, vacuum gas oils, demetalized oils, naphtha streams, or combinations of these.

A twenty-sixth aspect of the present disclosure may include any of the thirteenth through twenty-fifth aspects, further comprising mixing the regenerated first catalyst and the greater boiling point fraction in a first mixing zone positioned upstream of a first cracking reaction zone of the first FCC unit and mixing the regenerated second catalyst with the lesser boiling point fraction in a second mixing zone positioned upstream of a second cracking reaction zone of the second FCC unit.

A twenty-seventh aspect of the present disclosure may include any of the thirteenth through twenty-sixth aspects, further comprising separating at least a portion of the first cracking reaction product from the spent first catalyst in a first separating zone before passing the spent first catalyst to the first regeneration zone, and separating at least a portion of the second cracking reaction product from the spent second catalyst in a second separating zone before passing the spent second catalyst to the second regeneration zone.

A twenty-eighth aspect of the present disclosure may include any of the thirteenth through twenty-seventh aspects, further comprising recycling the regenerated first catalyst back to the first cracking reaction zone of the first FCC unit and recycling the regenerated second catalyst back to the second cracking reaction zone of the second FCC unit.

A twenty-ninth aspect of the present disclosure may include any of the thirteenth through twenty-eighth aspects, further comprising passing the regenerated first catalyst from the first regeneration zone to a first catalyst feed hopper, and passing the regenerated second catalyst from the second regeneration zone to a second catalyst feed hopper.

A thirtieth aspect of the present disclosure may include any of the thirteenth through twenty-ninth aspects, where the first cracking reaction product or the second cracking reaction product comprises one or more of ethylene, propene, butene, or pentene.

A thirty-first aspect of the present disclosure may include any of the thirteenth through thirtieth aspects, further comprising stripping another portion of the first cracking reaction product from the spent first catalyst upstream of the first regeneration zone.

A thirty-second aspect of the present disclosure may include any of the thirteenth through thirty-first aspects, further comprising stripping another portion of the second cracking reaction product from the spent second catalyst upstream of the second regeneration zone.

A thirty-third aspect of the present disclosure may be directed to a system for producing at least one petrochemical product from a hydrocarbon material, the system including a first cracking reaction zone, a first separation zone downstream of the first cracking reaction zone, a first regeneration zone downstream of the first separation zone, a second cracking reaction zone in parallel with the first cracking reaction zone, a second separation zone downstream of the second cracking reaction zone, a second regeneration zone downstream of the second separation zone, and a flue gas flow path extending from the first regeneration zone to the second regeneration zone. The second regeneration zone may be physically separated from the first regeneration zone, and the flue gas flow path may comprise a particulate barrier for preventing a transfer of one or more spent catalysts between the first regeneration zone and the second regeneration zone.

A thirty-fourth aspect of the present disclosure may include the thirty-third aspect, further comprising a first mixing zone upstream of the first cracking reaction zone and in fluid communication with the first cracking reaction zone.

A thirty-fifth aspect of the present disclosure may include the thirty-fourth aspect, further comprising a first catalyst hopper disposed between and fluidly coupled with the first regeneration zone and the first mixing zone.

A thirty-sixth aspect of the present disclosure may include any of the thirty-third through thirty-fifth aspects, further comprising a second mixing zone upstream of the second cracking reaction zone and in fluid communication with the second cracking reaction zone.

A thirty-seventh aspect of the present disclosure may include the thirty-sixth aspect, further comprising a second catalyst hopper disposed between and fluidly coupled with the second regeneration zone and the second mixing zone.

A thirty-eighth aspect of the present disclosure may include any of the thirty-third through thirty-seventh aspects, further comprising a first stripping zone downstream of the first separation zone and fluidly coupled to the first separation zone.

A thirty-ninth aspect of the present disclosure may include any of the thirty-third through thirty-eighth aspects, further comprising a second stripping zone downstream of the second separation zone and fluidly coupled to the second separation zone.

A fortieth aspect of the present disclosure may include any of the thirty-third through thirty-ninth aspects, further comprising a feed separator having an inlet, a greater boiling point fraction outlet stream, and a lesser boiling point fraction outlet stream, where the greater boiling point fraction outlet stream is fluidly coupled to the first cracking reaction zone and the lesser boiling point fraction outlet stream is fluidly couple to the second cracking reaction zone.

A forty-first aspect of the present disclosure may include any of the thirty-third through fortieth aspects, further comprising a product separator fluidly coupled to the first separation zone, the second separation zone, or both the first separation zone and the second separation zone.

A forty-second aspect of the present disclosure may be directed to a process for producing one or more petrochemical products from a hydrocarbon feed stream, the process including separating the hydrocarbon feed stream into a lesser boiling point fraction and a greater boiling point fraction, cracking the greater boiling point fraction in a first fluid catalytic cracking (FCC) unit in the presence of a first catalyst and at a reaction temperature of from 500° C. to 700° C. to produce a first cracking reaction product, and cracking the lesser boiling point fraction in a second FCC unit in the presence of a second catalyst and at a reaction temperature of from 500° C. to 700° C. to produce a second cracking reaction product, the second FCC unit operated in parallel with the first FCC unit. The process further includes regenerating the first catalyst in a first regeneration zone, transferring heat from the first regeneration zone to the second regeneration zone, and regenerating the second catalyst in a second regeneration zone separate from the first regeneration zone. The process may further include recycling the first catalyst back to the first FCC unit and the second catalyst back to the second FCC unit and recovering the first cracking reaction product and the second cracking reaction product.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising." For the purposes of defining the present technology, the transitional phrase "consisting of" may be introduced in the claims as a closed preamble term limiting the scope of the claims to the recited components or steps and any naturally occurring impurities. For the purposes of defining the present technology, the transitional phrase "consisting essentially of" may be introduced in the claims to limit the scope of one or more claims to the recited elements, components, materials, or method steps as well as any non-recited elements, components, materials, or method steps that do not materially affect the novel characteristics of the claimed subject matter. The transitional phrases "consisting of" and "consisting essentially of" may be interpreted to be subsets of the open-ended transitional phrases, such as "comprising" and "including," such that any use of an open ended phrase to introduce a recitation of a series of elements, components, materials, or steps should be interpreted to also disclose recitation of the series of elements, components, materials, or steps using the closed terms "consisting of" and "consisting essentially of." For example, the recitation of a composition "comprising" components A, B and C should be interpreted as also disclosing a composition "consisting of" components A, B, and C as well as a composition "consisting essentially of" components A, B, and C. Any quantitative value expressed in the present application may be considered to include open-ended embodiments consistent with the transitional phrases "comprising" or "including" as well as closed or partially closed embodiments consistent with the transitional phrases "consisting of" and "consisting essentially of."

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a stream or in a reactor should be appreciated as containing, in some embodiments, a mixture of isomers of that constituent. For example, a compositional range specifying butene may include a mixture of various isomers of butene. It should be appreciated that the examples supply compositional ranges for various streams, and that the total amount of isomers of a particular chemical composition can constitute a range.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it should be apparent to those skilled in the art that various modifications and variations can be made to the described embodiments without departing from the spirit and scope of the claimed subject matter. Thus, it is intended that the specification cover the modifications and variations of the various described embodiments provided such modification and variations come within the scope of the appended claims and their equivalents.

What is claimed is:

1. A process for producing petrochemical products from upgrading a hydrocarbon material, the process comprising:
    separating the hydrocarbon material into a lesser boiling point fraction and a greater boiling point fraction;
    cracking at least a portion of the greater boiling point fraction in the presence of a first catalyst at a reaction temperature of from 500° C. to 700° C. to produce a first cracking reaction product and a spent first catalyst;
    cracking at least a portion of the lesser boiling point fraction in the presence of a second catalyst at a reaction temperature of from 500° C. to 700° C. to produce a second cracking reaction product and a spent second catalyst;
    separating at least a portion of the first cracking reaction product from the spent first catalyst;
    separating at least a portion of the second cracking reaction product from the spent second catalyst;
    regenerating at least a portion of the spent first catalyst to produce a regenerated first catalyst, wherein regenerating the portion of the spent first catalyst comprises contacting the portion of the spent first catalyst with combustion gases in a first riser and passing the portion of the spent first catalyst and the combustion gases to a first regeneration zone downstream of the first riser;
    maintaining the spent second catalyst separate from the spent first catalyst;
    transferring heat from regeneration of the spent first catalyst to the spent second catalyst;
    regenerating at least a portion of the spent second catalyst to produce a regenerated second catalyst, wherein regenerating the portion of the spent second catalyst comprises contacting the portion of the spent second catalyst with combustion gases in a second riser and passing the portion of the spent second catalyst and the combustion gases to a second regeneration zone downstream of the second riser; and recovering the first cracking reaction product and the second cracking reaction product.

2. The process of claim 1 further comprising contacting the spent second catalyst with a flue gas from regeneration of the first spent catalyst.

3. The process of claim 1 where the first catalyst is different than the second catalyst.

4. The process of claim 1 where the hydrocarbon material comprises at least one of a crude oil, vacuum residue, tar sands, bitumen, atmospheric residue, vacuum gas oils, demetalized oils, naphtha, or combinations of these.

5. The process of claim 1 where the first cracking reaction product or the second cracking reaction product comprises at least one of ethylene, propene, butene, or pentene.

6. The process of claim 1 further comprising:
recycling the regenerated first catalyst back into contact with the greater boiling point fraction; and
recycling the regenerated second catalyst back into contact with the lesser boiling point fraction.

7. The process of claim 1, where the spent first catalyst and the combustion gases are passed into a top portion of the first regeneration zone and the spent second catalyst and the combustion gases are passed into a top portion of the second regeneration zone.

8. The process of claim 1, where only the spent first catalyst and the combustion gases are passed to the first riser and only the spent second catalyst and the combustion gases are passed to the second riser.

9. The process of claim 1, where a weight ratio of the first catalyst to the greater boiling point fraction is from 3:1 to 15:1.

10. A process for operating a hydrocarbon feed conversion system having a first fluidic catalytic cracking (FCC) unit and a second FCC unit, the process comprising:
introducing a hydrocarbon feed stream to a feed separator;
separating the hydrocarbon feed stream into a lesser boiling point fraction and a greater boiling point fraction in the feed separator;
passing the greater boiling point fraction to the first FCC unit;
passing the lesser boiling point fraction to the second FCC unit;
cracking at least a portion of the greater boiling point fraction in first FCC unit in the presence of a first catalyst at a reaction temperature of from 500° C. to 700° C. to produce a first cracking reaction product and a spent first catalyst;
cracking at least a portion of the lesser boiling point fraction in the second FCC unit in the presence of a second catalyst and at a reaction temperature of from 500° C. to 700° C. to produce a second cracking reaction product and a spent second catalyst;
contacting at least a portion of the spent first catalyst with combustion gases in a first riser of the regenerator;
passing the portion of the spent first catalyst and combustion gases from the first riser to a top portion of a first regeneration zone;
regenerating the portion of the spent first catalyst in the first regeneration zone to produce a regenerated first catalyst;
contacting at least a portion of the spent second catalyst with combustion gases in a second riser of the regenerator;
passing the portion of the spent second catalyst and combustion gases from the second riser to a top portion of a second regeneration zone separate from the first regeneration zone;
regenerating the portion of the spent second catalyst in the second regeneration zone to produce a regenerated second catalyst;
transferring heat from the first regeneration zone to the second regeneration zone;
recycling the regenerated first catalyst to the first FCC unit and the regenerated second catalyst to the second FCC unit; and
recovering the first cracking reaction product and the second cracking reaction product.

11. The process of claim 10 further comprising:
passing a flue gas stream from the first regeneration zone to the second regeneration zone; and
contacting the spent second catalyst in the second regeneration zone with the flue gas stream.

12. The process of claim 10 further comprising maintaining the spent first catalyst in the first regeneration zone separate from the spent second catalyst in the second regeneration zone.

13. The process of claim 10 where the second regeneration zone is separated from the first regeneration zone by a porous separation zone.

14. The process of claim 10 further comprising:
restricting flow of the spent first catalyst from the first regeneration zone to the second regeneration zone; and
restricting flow of the spent second catalyst from the second regeneration zone to the first regeneration zone.

15. The process of claim 10 where the first regeneration zone and the second regeneration zone are disposed within a single regenerator.

16. The process of claim 10 where the first catalyst is different than the second catalyst.

17. The process of claim 10 further comprising:
separating at least a portion of the first cracking reaction product from the spent first catalyst in a first separating zone before passing the spent first catalyst to the first regeneration zone; and
separating at least a portion of the second cracking reaction product from the spent second catalyst in a second separating zone before passing the spent second catalyst to the second regeneration zone.

18. The process of claim 10 further comprising recycling the regenerated first catalyst back to a first cracking reaction zone of the first FCC unit and recycling the regenerated second catalyst back to a second cracking reaction zone of the second FCC unit.

19. The process of claim 10 further comprising:
passing the regenerated first catalyst from the first regeneration zone to a first catalyst feed hopper; and
passing the regenerated second catalyst from the second regeneration zone to a second catalyst feed hopper.

* * * * *